United States Patent [19]
Hu

[11] Patent Number: 6,004,969
[45] Date of Patent: Dec. 21, 1999

[54] TRANSDERMAL DELIVERY OF BUPRENORPHINE PREPARATIONS

[75] Inventor: Oliver Yoa-Pu Hu, Taipei, Taiwan

[73] Assignee: National Science Council, Taipei, Taiwan

[21] Appl. No.: 08/948,234

[22] Filed: Oct. 9, 1997

Related U.S. Application Data

[63] Continuation of application No. 08/632,605, Apr. 15, 1996, abandoned.

[51] Int. Cl.$^6$ .............................. A61K 31/44; A61L 15/00
[52] U.S. Cl. .......................... 514/282; 514/279; 514/558; 514/947; 424/445; 424/448; 424/449
[58] Field of Search ..................................... 514/279, 558, 514/282, 947; 424/445, 448, 449

[56] References Cited

U.S. PATENT DOCUMENTS

| | | | |
|---|---|---|---|
| 5,069,909 | 12/1991 | Sharma et al. ........................... | 424/449 |
| 5,240,932 | 8/1993 | Morimoto et al. ....................... | 514/282 |

OTHER PUBLICATIONS

HCAPLUS abstract 1994: 62109 (1994) Roy, S. D. et al.
HCAPLUS abstract 1995: 795336 (1993) Friedman, D. et al.

*Primary Examiner*—M. Moezie
*Attorney, Agent, or Firm*—Bucknam and Archer

[57] ABSTRACT

Buprenorphine is a potent analgesic agent, it has been shown to be as effective as morphine. The main clinical application of buprenorphine is to relief postoperative pains or for patients in the terminal phase of cancer. The chance of becoming addiction and abuse is low, therefore it is pretty safe for clinical use. The half life of buprenorphine is short, since its hepatic extraction (extraction ratio is 0.7 to 0.9) and metabolism are high. For these reasons, oral administration of buprenorphine becomes impractical due to the need of giving drug frequently. The present invention is related to enhancers used in transdermal preparations of narcotic analgesic agents. This invention employs pure components of Chinese herbs in a fixed ratio as transdermal penetration enhancers. Compositions of these transdermal preparations usually include 0.1 to 50% of narcotic analgesic agent, 0.1 to 70% of pure components from Chinese herb as transdermal penetration enhancers, and other necessary excipients for transdermal delivery. Studies for the present invention in nude mice revealed that a transdermal preparation containing 10% of terpineol can delivery 15 mg of buprenorphine through 10 cm$^2$ skin area in 48 hours, which satisfied the need of practical use.

6 Claims, 22 Drawing Sheets

TRANSDERMAL DELIVERY OF BUPRENORPHINE PREPARATIONS

This application is a continuation of applicaiton Ser. No. 08/632,605, filed Apr. 15, 1996, now abandoned which application is entirely incorporated herein by reference

DETAILED DESCRIPTION

1. Description of the Prior Art

The chemical name of Buprenorphine is 21-cyclopropylmethyl-7-α-[(S)-1-hydroxy-1,2,2-trimethylpropyl]-6,14-endoethano-6,7, 8,14-tetrahydroripavine. It is a semi-synthesized hydrophobic derivative of thebaine. It is an analgesic agent which serves as a mu-receptor agonist and a kappa receptor antagonist. Similarly to morphine, buprenorphine exerts analgesic function in central nervous system (CNS). At present, the common routes for administration of marketed buprenorphine preparations include sublingual, intravenous (IV), intramuscular (IM), and spinal injection. Oral administration of buprenorphine is impractical due to poor gastrointestinal absorption, a high hepatic extraction ratio about 0.7 to 0.9, and a high first pass effect.

Morphine-like analgesic agents include codeine, alphaprodine, butorphanol, anileridine, hydromorphone, buprenorphine, fentanyl, levorphanol, hydrocodone, propoxyphene, meperidine, nalbuphine, methadone, levallorphan, pentazocine, oxymorphone, naltrexone, nalmefene, morphine, oxycodone, naloxone, opium, and nalorphine. Their structures are shown in FIG. (1).

Transdermal delivery is a controlled drug delivery system. It controls the release of drug continuously to the surface of skin, then the drug penetrates skin and enters capillary blood circulation system. Blood circulation later brings the drug to the target organ and exerts its action. The advantage of transdermal drug delivery is its convenience and ease of removing away from skin, thus the chance of dose dumping is minimized. In general, the surface area of an adult is 2 square meter, and capillary blood flowing throughtout body surface area accounts for one third of the whole blood circulation, this offers an unique advantage for transdermal drug delivery system. In addition, transdermal drug delivery system not only avoids some side effects of traditional preparations, but also controls the release of drug. For these reasons, transdermal drug delivery system is practical in clinical use.

Some physical and chemical properties of a drug, such as concentration, partition coefficient, molecular weight, and polarity may affect the efficiency of transdermal drug delivery. Other physical and chemical factors of the transdermal system, such as the polarity of the base, the solubility of drug in the base, the compositions in the preparation, and the viscosity of each component may also affect the efficiency of drug delivery. In addition, the physiological or pathological condition of the skin, lipoid membrane of the skin surface, hydration condition and the temperature of the skin, different sites of the skin, trauma, injury, and possibility of metabolism may also affect the transdermal drug delivery. At the present time, the most common problem for a transdermal drug delivery system is the lack of safe enhancers. It is proposed that the use of pure components from popular Chinese herbs as enhancers would offer a strong potential future for transdermal drug delivery system.

Previous studies of transdermal delivery of buprenorphine were presented by Sharma, Ket al. (pp.464–5) and Nightingale, J., et al. (pp. 246–7) in 19th Proc. In. Symp. Controlled Release Bioact. Mater., or revealed in German patent 3939376 C1, European patent No.368409 A2, No. 432945 A1, and No. 368406A2. However, these transdermal systems of buprenorphine did not include any of pure components from Chinese herbs used according to the present invention.

In recent years, the orient medicine has been studied frequently by people due to the progressive development in medical studies. For example, the Health Department of Japan agreed in 1975 to include 210 herbal medications in National Health Insurance. According to a survey of doctor's prescriptions of herbal medications, the rank of usage frequency was in the following order: Glycyrrhizae Radix (71.4%), ZingiberisRhizoma(42.9%), Hoelen(35.2%), Paeoniae Radix(32.9%), Zizyphi Fructus(31.9%), Cinnamoni Cortex et Caulis(29.5%), etc. Besides ' among the 93 complex prescriptions, Glycyrrhizae Radix is the top popularity in the second edition of National Formulary of Japan, and Zingiberis Rhizoma is the second. Others were similar to those that in the list of Nation Health Insurance.

Herbs used in high frequencies in complex herbal medicine are Glycyrrhizae Radix, Cinnamoni Cortex et Caulis, Zizyphi Fructus, Benzoinum, Zingiberis Rhizoma, Zedoariae Rhizoma, Magnoliae Flos, Achyranthis Radix, Foeniculi Fructus, Eucalypti Folium, Cardamomi Fructus, Zanthoxyli Fructus, Lupuli Strobilus, Magnoliae Cortex, Cinae Flos, Perillae Herba, Valerianae Radix, Asari Herbacum Radice, Menthae Herba, Myristicae Semen, Amomi Cardamomi Fructus, Piperis Fructus, Corni Fructusus, Benzoinum, etc. Due to the differences in original places and harvest seasons, the contents of some compositions are not the same, or may even opposite.

Some compositions in herbs possess surface active properties, which may lower the surface tension of human skin, and thus help drugs penetrate the skin and reach the deeper end of epidermis tissue, resulting in highly therapeutic efficacy. For instance, topical use of glycyrrhizic acid and glycyrrhetinic acid can inhibit animal paw swelling.

SUMMARY OF THE INVENTION

The object of the invention is to provide a transdermal preparations compositions of narcotic analgesic agents.

The further object of the invention is to provide compositions of these transdermal preparations usually comprise 0.1 to 50% of narcotic analgesic agent, 0.1 to 70% of pure components from Chinese herb as transdermal penetration enhancers, and other necessary excipients for transdermal delivery.

The present invention employs those herbs which appeared in herbal medications with high frequencies. These herbs which are shown in Table 2~4, are similar to the 210 kinds of complex herbal prescriptions covered by the Nation Health Insurance issued by Japan Health Department. For instance, Glycyrrhizae Radix, Cinnamoni Cortex et Caulis, Benzoinum, Zingiberis Rhizoma, Zizyphi Fructus, Zedoariae Rhizoma, Magnoliae Flos, Achyranthis Radix, Foeniculi Fructus, Eucalypti Folium, Cardamomi Fructus, Zanthoxyli Fructus, Lupuli Strobilus, Magnoliae Cortex, Cinae Flos, Perillae Herba, Valerianae Radix, Asari Herbacum Radice, Menthae Herba, Myristicae Semen, Amomi Cardamomi Fructus, Piperis Fructus, Corni Fructusus. These herbs belong to 50 aceaces and 400 genus. In order to use these herbs for transdermal enhancers, purified compositions are needed. Since these purified compositions are obtained after extraction, isolation, and purification, structure and purity are well recognized, e.g. glycyrrhizin and (lS)-(–)-α-Pinene are highly purified, therefore, place or origin and harvest season do not affect the purity. Some plants, such as Cuphea liavea, contains capric acid. The method for isolation and purification of the capric acid was already described in U.S. Pat. No. 2,964,546, and its synthesis from octyl bromide was shown by Shishido in 1959 in J. Am. Chem. Soc. 81, pp.5817.

The present invention "transdermal delivery of buprenorphine preparations" includes a narcotic analgesic agents from 0.1% to 50%, drug enhancers from 0.1% to 70%, and other excipients from 0.01% to 99.95% necessary for transdermal preparations. Those necessary excipients mentioned in this invention wherein the excipients selected from one of the compounds of stearyl alcohol, sodium carboxymethylcellulose, glycerol, cetyl alcohol, 1,3-propylene glycol and water. The present invention includes preparations in the forms of ointment, suspension, gel, solution, cream, lotion, emulsion, plaster, aerosol for local applications. The narcotic analgesic agents in the present invention include morphine-like analgesic agents, whose structures are listed in Table 1. These narcotic analgesic agents are commonly presented as buprenorphine, codeine, nalorphine, nalbuphine, methadone, fentanyl, morphine, oxycodone, naloxone, propoxyphene, opium, oxymorphone, meperidine, naltrexone, pentazocine, levallorphan, and butorphanol.

The transdermal diffusion test apparatus used by this invention is a vertical franz cell, as shown in FIG. (1). The apparatus includes a set of vertical containers that have double layers of glasses, the upper layer and lower layer can be separated. The lower container is filled with fixed amount of 0.02 M phosphate buffer, and a stirring bar to make the solution homogeneously. The space between outer and inner walls are circulated with water to maintain constant temperature. A sample of 0.5 g is placed in the upper container, the top opening is covered by plastic film. A layer of animal skin, such as abdomen skin from nude mice, skin from human leg or foot, or abdomen skin from rabbits is placed in between the upper and lower parts to act as a diffusion barrier. This skin layer is fixed by a metal clamp. At preset time intervals, 200 a 1 of phosphate buffer was drawn via the sampling port, and then replaced with same volume of fresh phosphate buffer. Each sample was added to 200 $\mu$l of 5-$\mu$g/ml nalbuphine as internal standard for the HPLC assay. The contents of samples were calculated by a calibration curve, and the amounts of drug released from the preparation can be correctly obtained.

To test the suitability of morphine structural analogs for the present invention, buprenorphine was selected as the model drug. A HPLC with fluorescence detector was used to validate the method for analysis. First, abdomen skins from nude mice were selected to compare the differences in transdermal permeation between buprenorphine hydrochloride (S9) and buprenorphine free base (S10) solutions. Based on the time curve indicated in FIG. (2), the result showed that the lag time of permeation of buprenorphine hydrochloride was statistically less than that of buprenorphine free base. The amount of penetration, permeation constant, and penetration rate are higher for This that indicates a hydrochloride salt of a hydrophobic drug has better transdermal absorption. Thus, the present invention selected buprenorphine hydrochloride as the model drug to develop the transdermal delivery system.

The present invention is applicable to buprenorphine and morphine analogs. Several pure components from a variety of herbs with different ratios were selected as transdermal absorption enhancers. These enhancers were one or combinations from the followings: pinene, 18-$\beta$-glycyrrhetinic acid, capric acid, glycyrrhizin, oleanolic acid, cincol, trans-cinnamic acid, $\beta$-myrcene, terpineol, trans-cinnamaldehyde, camphene, and palmitic acid. All of these enhancers are present in plants. For example, pinene, which is present in Eucalypti Folium, is further distinguished by different structures as a form and $\beta$ form, or (−)-$\alpha$, (+)-$\alpha$, and (+)-,$\beta$ forms. A herb may contain one form or all forms of pinene. For example, Valeriae Radix, Amomi Cardamomi Fructus, and Magnoliae Cortex have a form and $\beta$ form of pinene, Asari Herba and Piperis Fructus have $\beta$ form of pinene, Perillae Herba, Menthae Herba, and Zingiberis Rhizoma have $\alpha$ form of pinene, Cinae Flos has (−)$\alpha$- form of pinene, Myristicae Semen has (+)-$\alpha$ form and (+)- form of pinene, and Foeniculi Fructus has (+)-$\alpha$ form of pinene. 18-$\beta$-glycyrrhetinic acid and glycyrrhizin are present in Glycyrrhizae Radix. Oleanolic acid exists in Forsythiae Fructus, Corni Fructus, Caryophylli Flos, and Ziziphyi Fructus. Cineol, which is present in Zingiberis Rhizoma, Cardamomi Fructus, Eucalypti Folium, Magnoliae Flos, and Zedoariae Rhizoma, can be further distinguished as 1,8-Cincol or 1,4-Cincol. 1,8-Cincol exists in Amomi Cardamomi Fructus, Eucalypti Folium, and Magnoliae Flos. 1,4-Cicol exists in Zedoariae Rhizoma. $\beta$-mycrene exists in Hupulis Strobilus, Amomi Cardamomi Fructus, and Zingiberis Rhizoma. Terpineol exists in Cinae Flos, Valerianae Radix, and Eucalypti Folium. The structures of terpienol are further distingished as $\alpha$ form and $\beta$ form. The $\alpha$ form form is present in Myristicae Semen and Valerianae Radix; (+)-$\alpha$-terpineol is present in Cardamomi Fructus. Trans-cinnamic acid is present in Benzoinum. Trans-cinnamaldehyde exists in Cinnamoni Cortex et Caulis. Camphene exists in Magnoliae Cortex, and Menthae Herba, and its structure is also further distinguished as (+) and (−) froms. (+) Camphene exists in Myristicae Semen and Amomi Cardamomi Fructus; (−) camphene is present in Cinae Flos. Palmitic acid is present in Bupleuri Radix, Mori Cortex, and Coicis Semen.

The preparation of the present invention "transdermal delivery of buprenorphine preparations" contains 0.01% to 99.5% of any one of sodium carboxymethylcellulose, 1,3-propylene glycol, stearyl alcohol, cetyl alcohol, water and glycerin as the necessary excipients, mixed with 0.1% to 70% of pure compositions selected from one or more of the compounds of herbs mentioned previously as the enhancers, and 0.1% to 50% of the narcotic analgesic agents. As shown in FIGS. 5 to 9, gels, solutions, and creams were prepared.

Several gels (G1 to G4) were prepared with a variety of concentrations of buprenorphine, and the skin permeation of these gels are test on the abdomen skin of nude mice. As shown in FIG. 3, the results showed that the amount of penetration through the skin for 2.5 mg/ml buprenorphine HCl was 604 $\mu$g/cm2, which was 5.5 times higher than 1.0 mg/ml buprenorphine HC1, whose penetration was 110 $\mu$g/cm$^2$. It is concluded that increasing the concentration of buprenorphine hydrochloride also increases the amount of penetration. However, this correlation is not linear. When 5 to 70% w/w of 1,3-propylene glycol were added to buprenorphine gels(G5 to G10), the amount of skin penetration for buprenorphine was increased proportionally to the amount of propylene glycol in the formulation. The amount of skin penetration for the groups containing 60% and 70% of 1,3-propylene glycol were 1.5 times higher than the control group. When buprenorphine oleaginous creams containing 10 to 40% of 1,3-propylene glycol(E1 to E4) were tested, as shown in FIG. 5, the amount of penetration was also increased proportionally to the amount of 1,3-propylene glycol.

Results of the present invention applied to buprenorphine hydrochloride with pure substances from herbs as enhancers in the solution of 1, 3-propylene glycol were shown in FIG. 6. Solutions containing 10% w/w of β-myrcene as enhancer (S2) result in eight times higher penetration than the control group (S1). In FIG. 6 and 7, solutions containing (+)-α-pinene as enhancer(S5) resulted in five times higher penetration than the control group (S1). With capric acid as enhancer (S3) the results are two times higher penetration than the control group (S1). Solution containing trans-cinnamaldehyde as enhancer (S7) gave similar results as capric acid.

When buprenorphine solutions were prepared with propylene glycol as the necessary excipient as the control solution (S11), enhancer such as β-myrcene was added at 10% w/w (S12), 15% w/w (S13), or enhancer such as terpineol was added 10% w/w (Sl4), or β-myrcene 10% w/w mixed with 10% w/w terpineol were added (S15). As shown in FIG. 8, the results indicated that 10% terpineol (S14) gave the highest penetration, and 10% 5-myrcene (S12) was the second. In Table 10, results showed that the amount of penetration through the abdomen skin of nude mice in 48 hours for the control solution (S11) was 35 μg/cm², for the S12 group was 1415 μg/cm² which was 40.4 times higher than the control group, and S13 was 711 μg/cm²(20.3 times), andforS14 group was 1546 μg/cm² (44.2 times).

When gels were prepared by mixing buprenorphine with 2% sodium carboxymethylcellulose and 20% of 1,3-propylene glycol as the control (G11), then 10% w/w of enhancers such as β-myrcene (from Zingiberis Rhizoma, Amomi Cardamomi Fructus, Lupuli Strobilus) (G12), trans-cinnamic acid (from Benzoinum) (G13), terpineol (G14), terpineol and myrcene (G15), and terpineol (G16) were added respectively. Results of the amount of penetration after 48 hours are shown in FIGS. 9 and 10. As shown in both figures, the penetration per unit area of the control (G11) was 175 μg/cm, G12 gel was 596μg/cm² which was 3.4 times of the control, G13 gel was 369 μg/cm² which was 2.1 times of the control, G14 gel was 965 μg/cm² which was 5.5 times of the control, G15 gel was 1193 μg/cm² which was 6.8 times of the control, and G16 gel was 1145 μg/cm² which was 6.5 times of the control.

When comparison was made between solutions in FIG. 8 and gels in FIG. 9, results were shown in FIG. 10. The result indicated that 10% w/w terpineol (S14) was the best enhancer, and 10% of β-myrcene (S12) was the second. Although solution containing 10% terpineol (S14) had the best skin penetration, which was 44.2 times higher than the control group (S11), a shorter lag time was found in solutions containing β-myrcene (S12 and S13). In summary, 1,3-propylene glycol solution containing 10% w/w terpineol can deliver 3.1 mg of buprenorphine hydrochloride through a 2 cm² transdermal patch every 48 hours on the abdomen skins of nude mice. Instead, 10% of β-myrcene solution can deliver 15 mg buprenorphine hydrochloride every 48 hours through a 10 cm² transdermal patch to satisfy the need of clinical treatment.

When rabbit abdomen skin was selected to compare the effects of enhancers, buprenorphine hydrochloride in 1,3-propylene glycol solution was used as control solution (S11), and 10% w/w of myrcene (S12) or 10% w/w myrcene mixed with same amount of terpineol (S15) was added to the control solution. Results were shown in FIG. 11, the accumulated amount of penetration for the control solution (S11) was 9 μg/cm², for S12 was 177 μg/cm² which was 19 times of the control solution, and for S15 was 2768 μg/cm² which was 301 times of the control solution. When 1,3-propylene glycol and PGFA were selected to prepare ointment as the control (O1), and 10% w/w of myrcene was added to the control ointment as the enhancer (O2), or 2% sodium carboxymethycellulose as the necessary excipient to prepare the control gel (G11), 10% w/w β-myrcene was added to the control gel as enhancer (G12), and 15% w/w terpineol was added to the control gel as enhancer (G16). Results of comparison between ointments and gels were shown in FIG. 12. The accumulated amount of buprenorphine HCl penetration for various ointments, gels and solutions through per unit of area of skin in 48 hours were listed in Table 11. The control ointment (O1) was 30 μg/cm, O2 was 46 μg/cm² which was 1.5 times of the control ointment, and the control gel (G11) was 162 μg/cm², G12 was 926 μg/cm² which was 5.7 times of the control gel, and G16 was 833 μg/cm² which was 5.1 times of the control gel.

When comparisons were made among solutions (FIG. 11), gels, and ointments (FIG. 12), results are shown in FIG. 13, the solution containing 10% w/w β-myrcene and same amount of terpineol as enhancers (S15) showed the best penetration, which was 301 times than the control one S11. This result indicated 1.1 cm² of β-myrcene solution can deliver 3.1 mg of buprenorphine every 48 hours. When gels were prepared by 2% sodium carboxymethylcellulose and 20% of 1,3-propylene glycol with various concentrations of buprenorphine, amounts of penetration in 48 hours were shown in FIGS. 14 and 15. Results showed that the highest penetration was the gel containing 0.8% w/w buprenorphine hydrochloride (G11), whose penetration amount was 162 g/cm², and this was 18 times control solution (S11), whose penetration was only 9 g/cm², and also was 5.4 times of ointment (O1), whose penetration was 30 μg/cm². When gels were prepared by 2% sodium carboxymethylcellulose and 20% of 1,3-propylene glycol with buprenorphine hydrochloride as the control (G11), 15% of β-myrcene was added as enhancer (G18), and 10% of β-myrcene was added as enhancer (G12), or terpineol was added in the amount of 10% w/w (G14), 15 % w/w (G16), 20% w/w (G21). Results of the amount of penetration in 48 hours are shown in FIG. 16 and Table 11. The control gel was 162 μg/cm², G12 gel was 926 jg/cm² which was 5.7 times of the control, G14 was 583 μg/cm²(3.6 times), G16 was 833 μg/cm² (5.1 times), G18 was 1362 μg/cm²(8.4 times), G21 was 604 μg/cm² (3.7 times). The result indicated 15% w/w terpineol was the beat enhancer, however, the effect was not more significant than β-myrcene.

When gels G11 was still the control, 15% w/w β-myrcene mixed with same amount of terpineol were added as enhancer (G20), or 20% w/w β-myrcene mixed with same amount of terpineol was added as enhancer (G30), or 15% w/w β-myrcene was added as enhancer (G18), or 20% of terpineol was added as enhancer (G21) respectively. Results of comparison are shown in FIG. 17 and Table 11. The amount of penetration per unit area in 48 hours for the control gel (G11) was 162μg/cm², G20 gel was 1127 μg/cm² which was 7.0 times of the control, G30 was 1008 μg/cm² (6.2 times), G18 was 1362 μg/cm²(8.4 times), G21 was 604 μg/cm²(3.7 times). The result indicated that 15% w/w β-myrcene had the best enhance effect. If β-myrcene was mixed with same amount of terpineol, a total amount of 20% was the best.

When gels were prepared by mixing 10% w/w β-myrcene with 10% w/w trans-cinnamic acid (G19), or 10% β-myrcene with the same amount of terpineol and trans-cinnamic acid (G17), 10% of trans-cinnamic acid (G13) , comparing to the control gel (Gl1), results of comparisons are shown in Table 18 and FIG. 11. The amount of penetration per unit area in 48 hours for the control G11 was 162 $\mu g/cm^2$, for G19 was 1343 $\mu g/cm^2$ which was 8.3 times of the control, for G17 was 1214 $\mu g/cm^2$(7.5 times), G13 was 116 $\mu g/cm^2$(0.7 times).

When gels were prepared by adding 10% w/w camphene (G31), or 5% w/w palmitic acid (G23), or 10% w/w Tween 80(G22) as enhancers, and compared to the control gel (G11), results of the amount of penetration tested on rabbit abdomen skin per unit area in 48 hours are showrn in FIG. 19 and Table 11. For the control G11, the amount of penetration was 162 $\mu g/cm^2$, for G31 gel was 250 $\mu g/cm^2$ which was 1.5 times of the control, for G23 was 138 $\mu g/cm^2$ (0.8 times), for G22 was 115 $\mu g/cm^2$(0.7 times).

To perform the study on human leg skin, the control solution (S11) was prepared by dissolving buprenorphine hydrochloride in 1.3-propylene glycol. 10% w/w β-myrcene was added as enhancer (S12), and 10% terpineol was also added as enhancer (S14). When human foot skin was used for the test, S11 was used as control, and 10% w/w terpineol was added as enhancer (S14). Results of accumulated amount of penetration per unit in 72 hours were shown in FIG. 20 and Table 12. The result for the control (S11) on leg skin was 1.2 $\mu g/cm^2$, and S12 was 16.4 $\mu g/cm^2$(14 times); on foot skin, S11 was 0.17 $\mu g/cm^2$, and S14 was 13.5 $g/cm^2$(81 times). On fresh human chest skin, the control G11 delivered 6.7 $\mu g/cm^2$ of buprenorphine hydrochloride. As shown in FIG. 21 and Table 12, gel containing 10% w/w β-myrcene and same amount of terpineol (G15), whose accumulated penetration amount was 87.6 $\mu g/cm^2$, which was 13.1 times of the control; gels containing 20% w/w terpineol (G21) was 33.0 $\mu g/cm^2$, which was 4.9 times of the control; gels containing 20% β-myrcene (G32) was 65.8 $\mu g/cm^2$ which was 9. 8 times of the control. From the above data, 1,3-propylene glycol solution containing 10% w/w β-myrcene delivered only 13.5 $\mu g/cm^2$ buprenorphine hydrochloride in 72 hours, whereas gels containing 10% w/w β-myrcene with the same amount of terpineol delivered 32.3 $\mu g/cm^2$ in 48 hour, and 65.8 $\mu g/cm^2$ in 72 hours.

For 1,3-propylene glycol solution containing buprenorphine hydrochloride (S11) and with 10% w/w β-myrcene as enhancer (S12), the penetration effect on nude mice abdomen skin was higher than human leg skin and rabbit abdomen skin, as shown in FIG. 22. For the control solution (S11), the accumulated amount of penetration per unit area in 48 hours on nude mice abdomen skin was 35 lig/cm² which was 3.9 times of the rabbit skin, as compared to 9 pg/cme on rabbit. In 72 hours, the accumulated amount of penetration on human leg skin was 0.12 $\mu g/cm^2$, human foot skin was 0.17 $\mu g/cm^2$. However, solution containing 10% w/w β-myrcene (S12) resulted in 1415 $\mu g/cm^2$ which was 8 times of 177 $\mu g/cm^2$ of rabbit skin, and in 72 hours, the accumulated amount of penetration on human leg skin was 16.4 $\mu g/cm^2$. From these data, rabbit skin was 13 to 33 times of human skin. It is estimated that only 10 to 30 cm² solution will be enough to deliver amount for actual use, if the best penetration per unit area on rabbit skin is replaced by human skin.

On nude mice abdomen skin, 1,3-propylene glycol solution containing 10% w/w terpineol (S14) gave the best result. In 48 hours, the accumulated amount of penetration per unit area was 44 times of the control (S11). However, solutions containing β-myrcene as enhancer had faster penetration with shorter lag time. On nude mice skin, every 2 cm² of 1,3-propylene glycol solution containing 10% w/w terpineol can deliver 3.1 mg in 48 hours ( if change to 10 cm² patch or solution, 15 mg of buprenorphine could be delivered every 48 hours) which satisfies the need for actual use. On rabbit abdomen skin, solution containing 15% w/w (S15) showed the best penetration effect, which was 301 times of the control (S11), this indicated that 1.1 cm² solution could deliver 3.1 mg of buprenorphine in 48 hours, this would satisfy the need for actual use. In fresh human chest skin model, gels containing 10% w/w β-myrcene with the same amount of terpineol could deliver 25.8 $\mu g/cm^2$ buprenorphine hydrochloride in 48 hours. This has been shown clinical usefulness.

The present invention related to buprenorphine transdermal preparations, of which 36 formulae were tested on the skin of nude mice. Results of 48 hours accumulated amount per unit area are listed in Table 10. Skin penetration of sixteen formulations including S2, 5, S512, S13, S14, G4, G12, G13, G14, G15, G16, El, E2, E3, E4, and E5 have shown statistical significance (p<0.001). Among each group, enhancers in the group S12, S13, S14 have the best enhance effects on penetration.

For the rabbit skin, 25 formulations were tested. Results were shown in Table 11 which indicated 10 formulations, including S15, G12, G14, G16, G17, G18, G19, G20, G21, and G30, have shown statistical significance (p<0.001) in the accumulated amount of penetration in 48 hours.As compared between groups, the enhancer in S15 has shown the best enhance effect on skin penetration.

Narcotic analgesic analogs of morphine derivatives are Codeine, Alphaprodine, Butorphanol, Anileridine, Hydromorphone, Opium, Buprenorphine, Morphine, Fentanyl, Levorphanol, Hydrocodone, Propoxyphene, Meperidine, Nalbuphine, Methadone, Levallorphan, Pentazocine, Oxymorphone, Naltrexone, Nalmefene, Oxycodone,Naloxone, and Nalorphine. Among them, Buprenorphine, Fentanyl, Pentazocine, Nalbuphine, Codeine, Morphine, Naloxone, Naltrexone, Butorphanol, Oxymorphone, and Meperidine are candidates of the active ingredient of transdermal preparation using the present invention. Enhancer of penetration can be one of the following: Glycyrrhizae Radix, Zingiberis Rhizoma, Amomi Cardamomi Fructus, Cardam-omi Fructus, Lupuli Strobilus, Myristicae Semen, Cyperi Rhizoma, Cinae Flos, Magnoliae Cortex, Zedoariae Rhizoma, ValerianaeRadix ,Menthae Herba, Piperis Fructus, Perillae Herba, Foeiculi Fructus, Zizyphi Fructus, Eucalypti Folium, Magnoliae Flos, CurcumaeRhizoma, Croci Stigm, Cinnamoni Cortex et caulis, Forsythiae Fructus, Caryophyllis Flos, Corni Fructusus, Benzoinum. The pure enhancers are the followings: β-myrcene, a-pinene, 18-β-glycyrrhetinic acid, terpineol, cineole, trans-cinnamaldehyde, capric acid, trans-cinnamic acid, palmitic acid, oleanolic acid and camphene.

In order to decribe this invention to the reader more obviously, the following application examples and figures are illustreted separatedly:

EXAMPLE 1 to 2

Preparation of solutions

S9 is prepared by dissolving 0.127% w/w of buprenorphine hydrochloride in water, and S10 is prepared by dissolving 0.118% w/w buprenorphine hydrochloride in water, the compositions are listed in table 5.

EXAMPLE 3

Preparation of solutions

The preparation of solution S1 is the same as example 1, except that 1.22% w/w buprenorphine is dissolved in 1,3-propylene glyclol.

EXAMPLE 4 to 10

Preparation of solutions

Buprenorphine is dissolved in 90% w/w 1,3-propylene glycol, with the addition of 10% w/w enhancer in accordance to Table 5. β-myrcene (from Zingiberis Rhizoma, Amoni Cardamoni Fructus, Lupuli Strobilus) is added in S2, cineole (from Zingiberis Rhizomaa, Cardamomi Fructus, Amomi Cardamomi Fructus, Eucalypti Folium, Zedoariae Rhizoma, Magnoliae Flos) is added in S4, capric acid is added in S3, β-glycyrrhetinic acid (from glycyrrhizae Radix) is added in S6, oleanolic acid (from Forsythiae Fructus, Caryophylli Flos, Zizyphi Fructus, Corni Fructusus) is added in S8, α-pinene (from Valaerianae Radix, Amomi Cardamomi Fructus, Magnoliae Cortex, Asari Herbacum Radice, Piperis Fructus, Perillae Herba, Menthae Herba, Zingiberis Rhizoma, Cinae Flos, Myristicae Semen, Foeniculi Fructus) is added in S5, trans-cinnamaldehyde (from Cinnamoni Cortex et caulis ) is added in S7. The details of compositions of S2 to S8 are shown in Table 5. In the preparation of S6 and S8, 100% w/w of 1,3-propylene glycol are used.

EXAMPLE 11 to 14

Preparation of gels 1 to 2.5% w/w of buprenorphine hydrochloride are dissolved in 50% w/w glycerin, following by the addition of 20% w/w sodium carboxymethylcellulose in a mortar. Then 50% w/w of water was added to prepare gels G1 to G4. Compositions of G1 to G4 are shown in Table 6.

EXAMPLE 15 to 20

Preparation of gels

Gels of G5 to G10 are prepared by dissolving 1% w/w of buprenorphine hydrochloride in different portions of glycerin and/or 1,3-propylene glycol, in accordance to Table 6. Then 20% w/w of sodium carboxymethylcellulose is added to each formula in a mortar. After mixing well, 30 to 50% w/w of water was added for further trituration.

EXAMPLE 21 to 24

Preparation of emulsions

Emulsions E1 to E4 are prepared by mixing buprenorphine HCl in oil of olay, following by adding different portions of 1,3-propylene glycol, in accordance to Table 7, to the mixture to ensure a completion of dissolving.

EXAMPLE 25 to 31

Preparation of gels

Gels of G11 to 16 are prepared in accordance to Table 8 by dissolving 0.8% w/w buprenorphine HCl in 20% w/w of 1,3-propylene glycol, then 10% of β-myrcene (from Zingiberis Rhizoma, Myristicae Semen, Lupuli Strobilus) or 10 to 15% w/w of terpineol (from Cardamomi Fructus, Myristicae Semen, Amomi Cardamomi Fructus, Cinae Flos) or 10% of trans-cinnamic acid (from Bezoinum), or combination of 10% of β-myrcene and 10% w/w of terpineol are added with 2% of sodium carboxymethylcellulose in the mortar. The control gel is prepared by dissolving 0.8% w/w of buprenorphine HCl in 20% of 1,3-propylene glycol with the addition of 2% w/w of sodium carboxymethylcellulose in themortar. Uponmixing, 66.7 to 77.2% w/wwater is added to the control (G11) gel.

EXAMPLE 32

Preparation of ointments 0.8% w/w of buprenorphine HCl is dissolved in 74.45% w/w of 1,3-propylene glycol which is at 75° C., then 18.6% w/w of stearyl alcohol, 6.19% w/w of cetyl alcohol are heated to 75° C., these two solutions are mixed thoroughly, and then the mixture is cooled to 25° C. with rapidly stirring to make ointment. The compositons are listed in Table 8.

EXAMPLE 33

Preparation of ointments

Similar to example 7, buprenorphine HCl is dissolved in 1,3-propylene glycol, with the addition of stearyl alcohol and cetyl alcohol. Then 10% w/w of β-myrcene (from Zingiberis Rhizome, Myristicae Semen, Lupuli Strobilus is added to the previous mixture. The final mixture is cooled to 25° C. to make ointment O2. The compositions are shown in Table 8.

EXAMPLE 34 to 38

Preparation of solutions

Solution S12 to S15 are prepared by dissolving 0.8% w/w of buprenorphine HCl in 80 to 90% w/w of 1,3-propylene glycol, then 10.15% w/w of β-myrcene (from Zingiberis Rhizoma, Myristicae Semen, Lupuli Strobilus) or 10% of terpineol (from Cardamomi Fructus, Amomi Cardamomi Fructusus, Myristicae Semen, Cinae Flos) or mixture of β-myrcene with the same amount of terpineol is added, and mixed well, following by centrifuge. The control solution S11 is prepared by dissolving 0.8% w/w of buprenorphine HCl in 100% w/w 1,3-propylene glycol, the composition are shown in Table 8.

EXAMPLE 39 to 44

Preparation of gels

Gels G24 to 29 are prepared by dissolved 0.4% to 3.2% w/w of buprenorphine HCl in 20% w/w of 1,3-propylene glycol, then add 2% w/w of sodium carboxymethylcellulose in the mortar. After homogenization, 74.8% to 77.6% w/w of water are added to prepare the final gels. The compositions are shown in Table 9.

EXAMPLE 45 to 53

Preparation of gels

Buprenorphine HCl is dissolved in 20% w/w of 1,3-propylene glycol, then follow the compositions in G17 to G23, or G30 to G32 in Table 9, by the addition of one or the combination of the following enhancers: in the amount of 10 to 20% w/w of β-myrcene, or 10 to 15% w/w of trans-cinnamic acid, or 10 to 20% w/w of terpineol, or 10% w/w of camphene, 5% w/w of palmitic acid, or 10% of Tween 80. Upon mixing, 2% w/w of sodium carboxymethlcellulose is added to the mixture, following by addition an appropriate amount of water to prepare homogenized gels.

Table 1. Structures of narcotic analgesic agents analogously to morphine

Table 2. Enhancers from Chinese herbs

Table 3. Enhancers from Chinese herbs
Table 4. Enhancers from Chinese herbs
Table 5. Compositions of solutions
Table 6. Compositions of gels
Table 7. Compositions of emulsions
Table 8. Compositions of transdermal preparations
Table 9. Compositions of transdermal preparations
Table 10. Results of transdermal penetration through the skin of nude mice
Table 11. Results of transdermal penetration throughout the skin of rabbits
Table 12. Results of transdermal penetration through the skin of human

Figure 1:
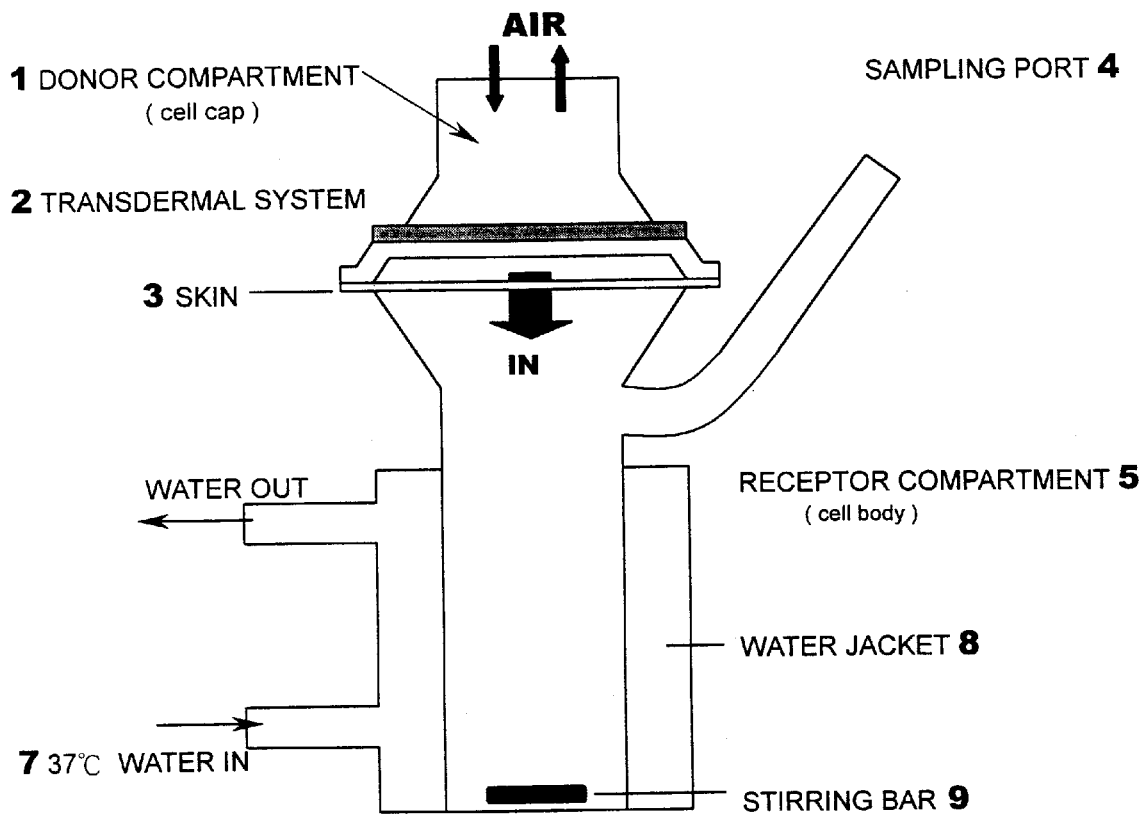
FIG. 1. Franz cell
(1.) containers for transdermal apparatus
(2.) transdermal delivery system
(3.) skin
(4.) sampling port
(5.) receiver of drug
(6.) water outlet
(7.) water inlet
(8.) water bath
(9.) stirrer FIG. 2.Transdermal penetration of buprenorphine HCl and free base in solutions
  S9 . . . buprenorphine hydrochloride
  S10 . . . buprenorphine free base FIG. 3. Transdermal penetration of gels with different concentration of buprenorphine HCl through the skin of nude mice
  G1 . . . 1.0 mg/ml
  G2 . . . 1.5 mg/ml
  G3 . . . 2.0 mg/ml
  G4 . . . 2.5 mg/ml FIG. 4. Amounts of penetration of buprenorphine HCl gels on the skin of nude mice FIG. 5. Amounts of penetration of buprenorphine HCl emulsions on the skin of nude mice FIG. 6. Transdermal penetration of buprenorphine HCl solutions on the skin of nude mice
  S1 . . . Control
  S2 . . . 10% w/w β-myrcene
  S3 . . . 10% w/w capric acid
  S4 . . . 10% w/w cineole FIG. 7. Transdermal penetration of buprenorphine HCl solutions on the skin of nude mice
  S5 . . . 10% w/w a-pinene
  S6 . . . 2% w/w β-glycyrrhetinic acid
  S7 . . . 10% w/w trans-cinnamaldehyde
  S8 . . . 2% w/w oleanolic acid FIG. 8. Effects of enhancers from Chinese herbs on the transdermal penetration through the skin of nude mice
  S14 . . . 10% w/w terpineol
  S12 . . . 10% β-myrcene
  S13 . . . 15% β-myrcene
  S11 . . . control of 1,3-propylene glycol group FIG. 9. Effects of enhancers from Chinese herbs on the transdermal penetration through the skin of nude mice
  G15 . . . 10% w/w β-myrcene and 10% w/w terpineol
  G16 . . . 15% w/w β-myrcene
  G14 . . . 10% w/w terpineol
  G13 . . . 10% w/w trans-cinnamic acid
  G12 . . . 10% w/w β-myrcene
  G11 . . . control of 20% w/w 1,3-propylene glycol and 2% sodium carboxymethylcellulose FIG. 10. Effects of enhancers from Chinese herbs on the transdermal penetration through the skin of nude mice
  S14 . . . 10% wlw terpineol
  S12 . . . 10% w/w β-myrcene
  G15 . . . 10% w/w β-myrcene and 10% w/w terpineol
  G16 . . . 15% w/w β-myrcene
  G14 . . . 10% w/w terpineol
  S13 . . . 15% w/w β-myrcene
  G12 . . . 10% w/w β-myrcene
  G13 . . . 10% w/w trans-cinnamic acid
  G11 . . . control of 20% w/w 1,3-propylene glycol and 2% sodium carboxymethylcellulose
  S11 . . . control of 1,3-propylene glycol group FIG. 11. Effects of enhancers from Chinese herbs on the transdermal penetration through the skin of rabbits
  S15 . . . 10% w/w β-myrcene and 10% w/w terpineol
  S12 . . . 10% w/w β-myrcene
  S11 . . . control of 20t 1,3-propylene glycol and sodium carboxymethylcellulose FIG. 12. Effects of enhancers from Chinese herbs on the trandermal penetration through the skin of rabbits
  G12 . . . 10% w/w β-myrcene
  G16 . . . 15% w/w terpineol
  G11 . . . control of 20% 1,3-propylene glycol and sodium carboxymethylcellulose
  O1 . . . PGFA ointment
  O2 . . . PGFA ointment with 10% w/w β-myrcene FIG. 13. Effects of enhancers from Chinese herbs on the transdermal penetration through the skin of rabbits
  S15 . . . 10% w/w β-myrcene and 10% w/w terpineol
  G12 . . . 10% w/w β-myrcene
  G16 . . . 15% w/w terpineol
  G11 . . . control of 20% 1,3-propylene glycol and sodium carboxymethylcellulose
  S12 . . . 10% w/w β-myrcene
  O2 . . . PGFA ointment with 10% w/w β-myrcene
  O1 . . . PGFA ointment
  S11 . . . 1,3-propylene glycol control FIG. 14. Effects of different concentrations of buprenorphine HCl with 2% sodium carboxymethylcellulose
  G11 . . . 0.8% buprenorphine Hcl
  G29 . . . 1.2% buprenorphine HCl
  G28 . . . 1.0% buprenorphine HCl
  G27 . . . 0.6% buprenorphine HCl
  G24 . . . 0.4% buprenorphine HCl
  G26 . . . 3.2% buprenorphine HCl
  G25 . . . 1.6% buprenorphine HCl FIG. 15. Penetration of Gels with various concentrations of buprenorphine HCl through the skin of rabbits
  G11 . . . 0.8% buprenorphine HCl
  G29 . . . 1.2% buprenorphine HCl
  G28 . . . 1.0% buprenorphine HCl
  G27 . . . 0.6% buprenorphine HCl G24 . . . 0.4% buprenorphine HCl
G26 . . . 3.2% buprenorphine HCl
G25 . . . 1.6% buprenorphine HCl FIG. 16. Penetration of buprenorphine HCl gels in 1,3-propylene glycol and sodium carboxymethylcellulose through the abdomen skin of rabbits.
Figure 2:
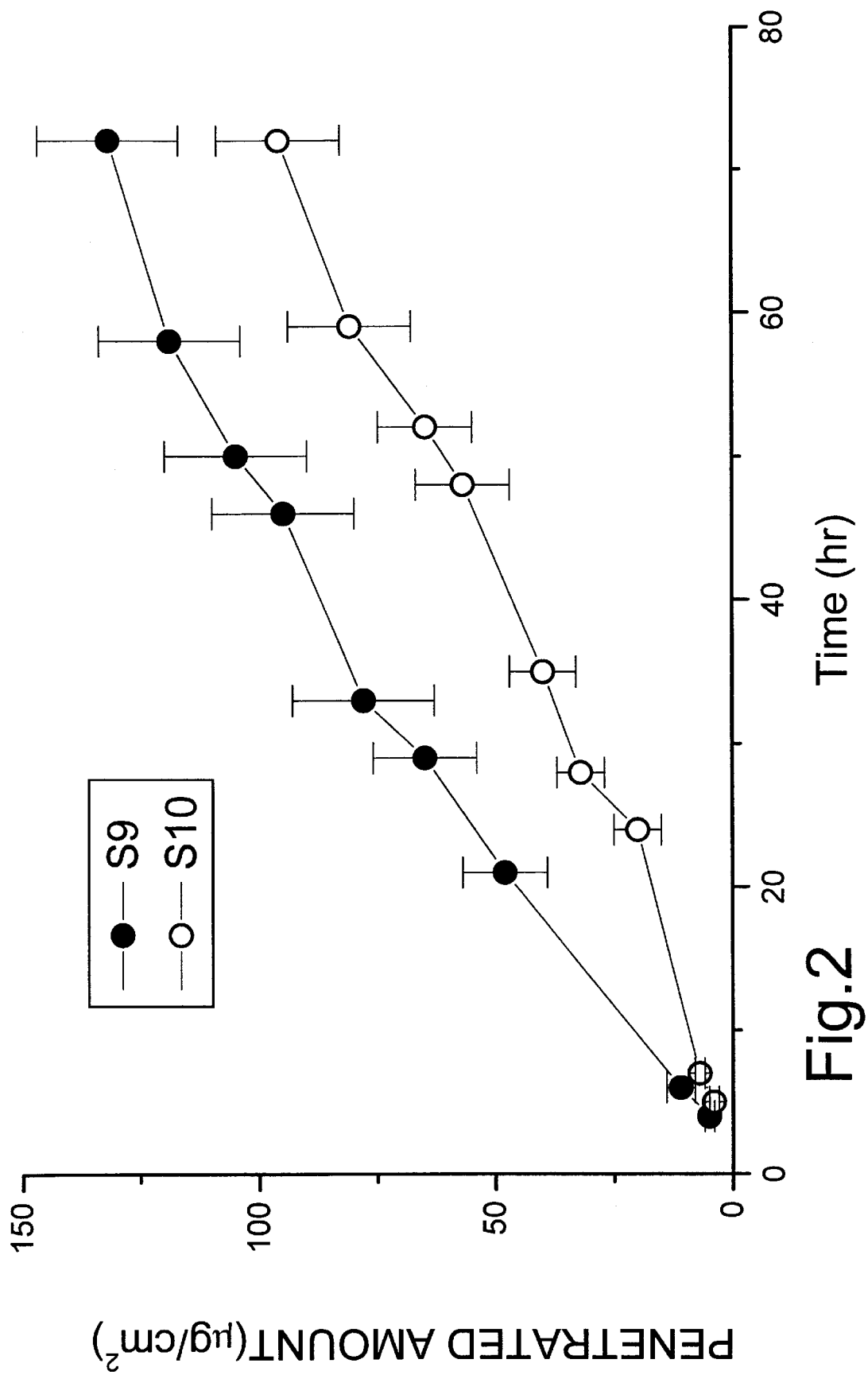
Figure 3:
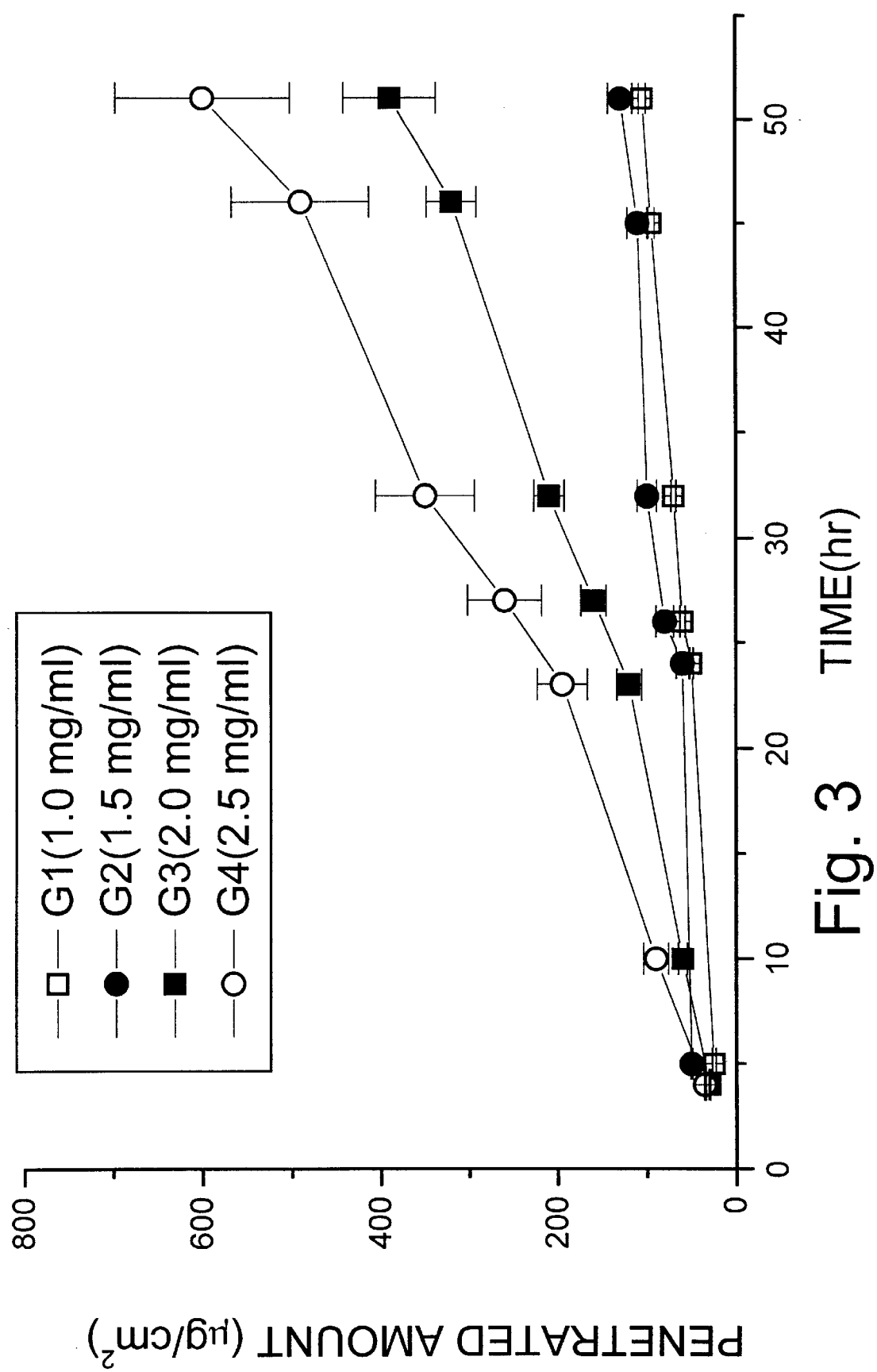
Figure 4:
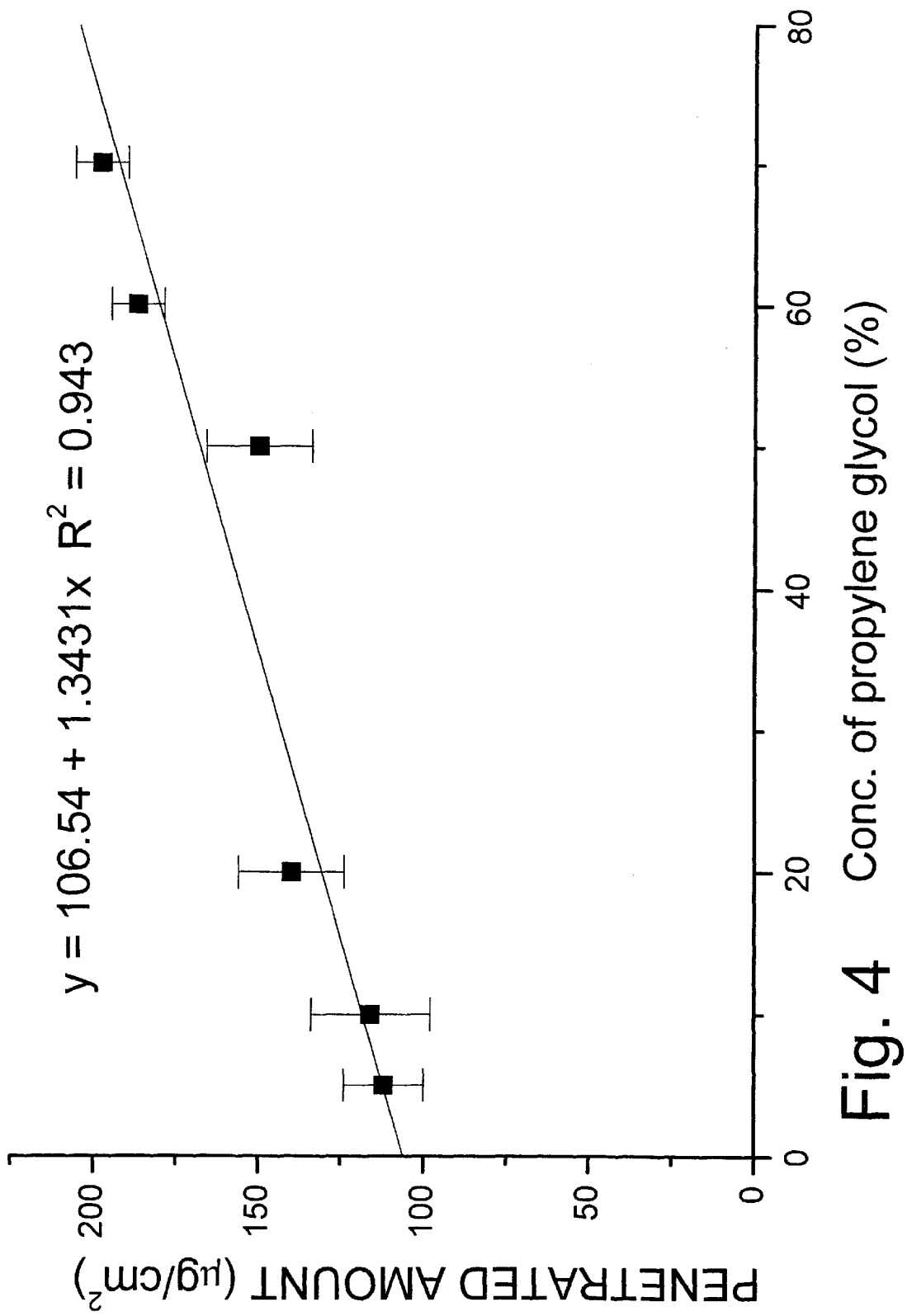
Figure 5:
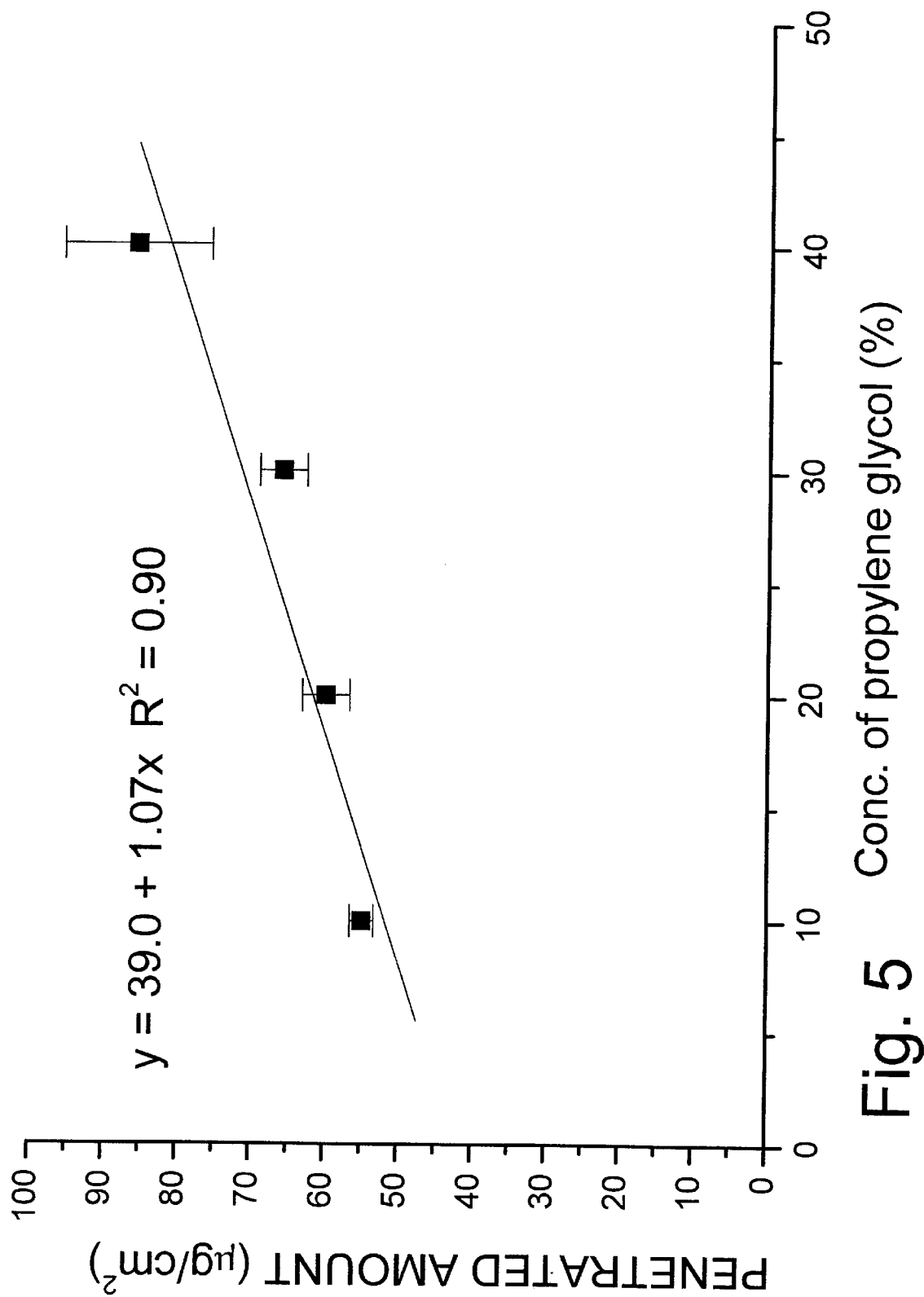
Figure 6:
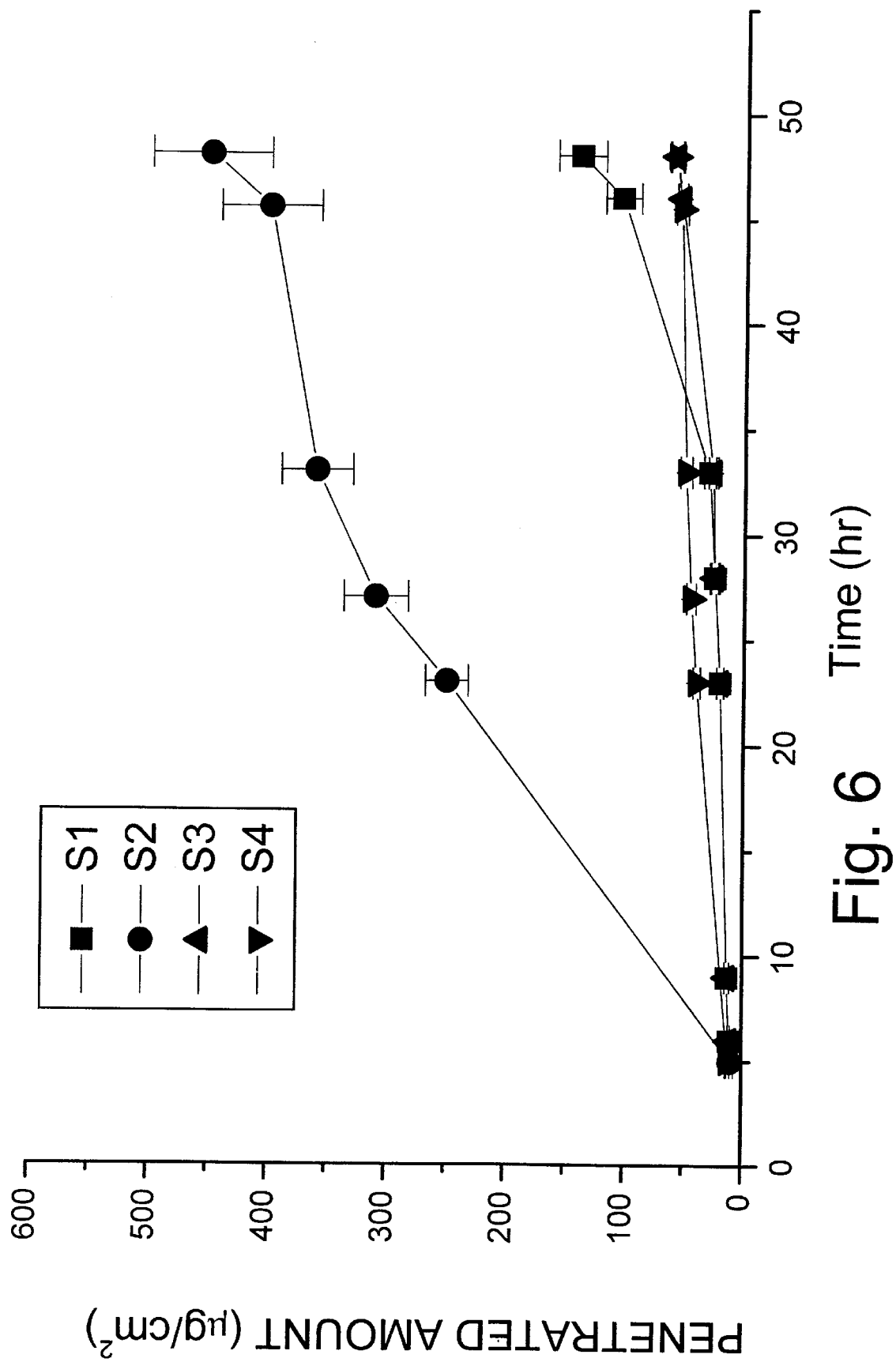
Figure 7:
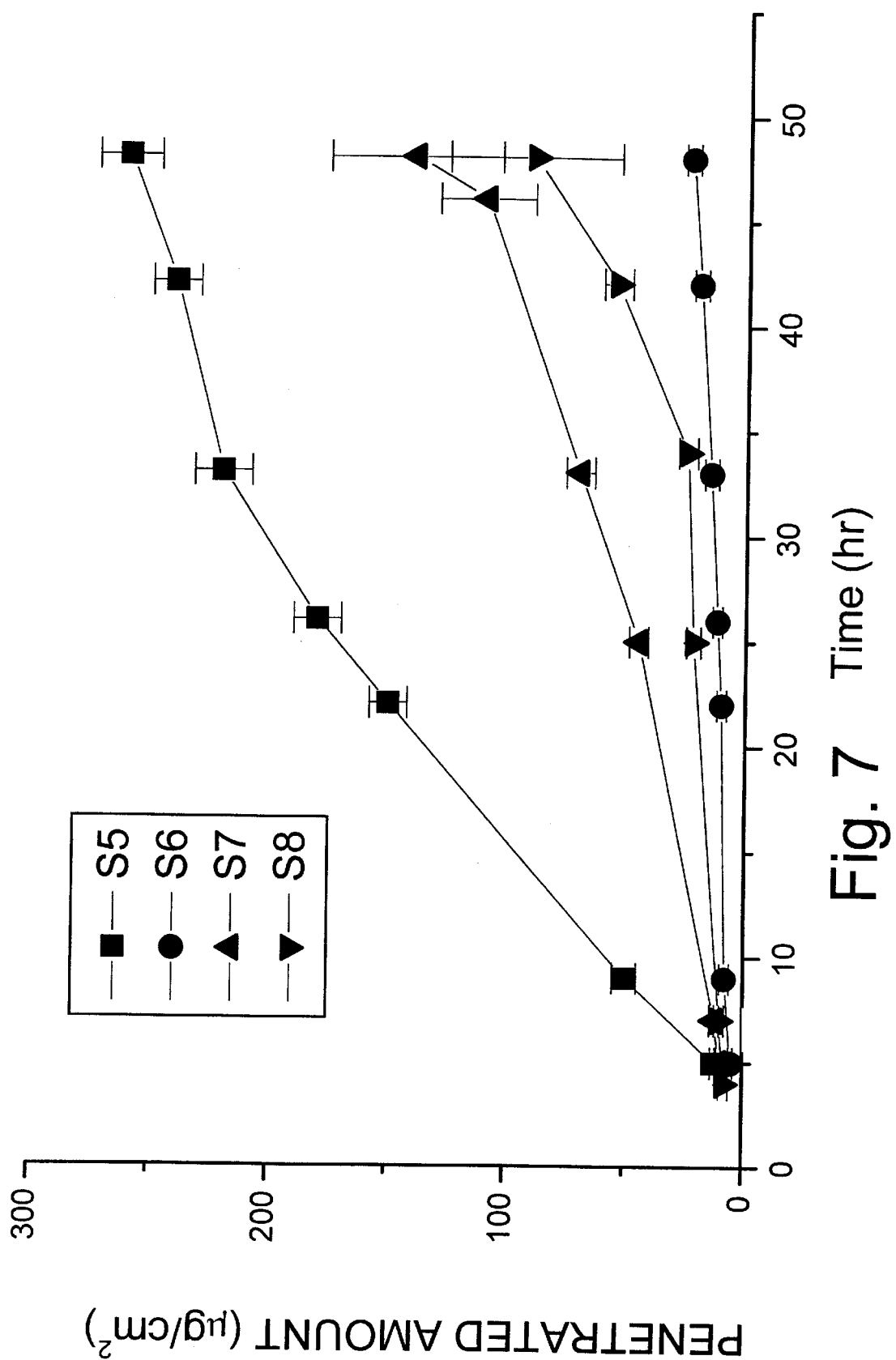
Figure 8:
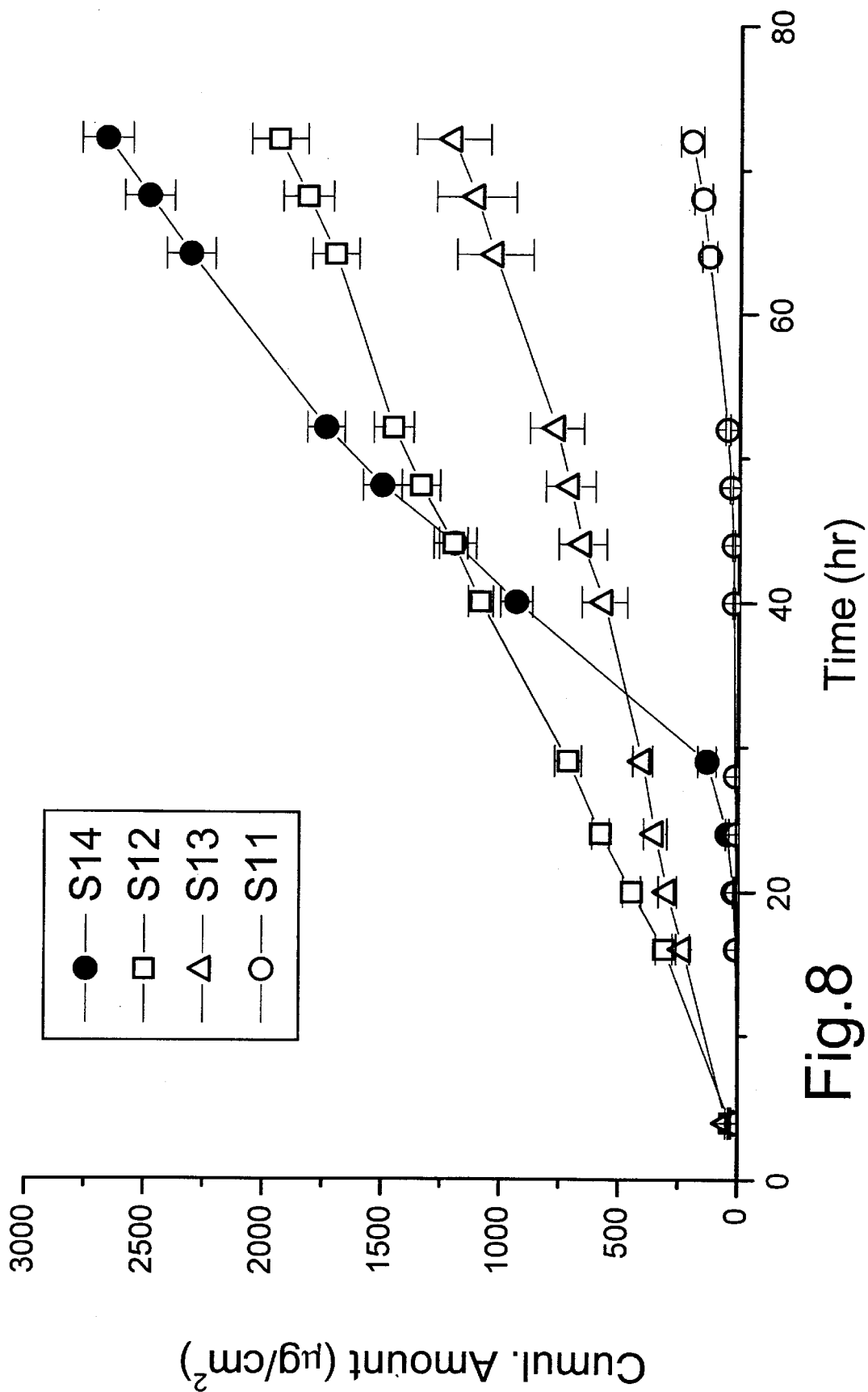
Figure 9:
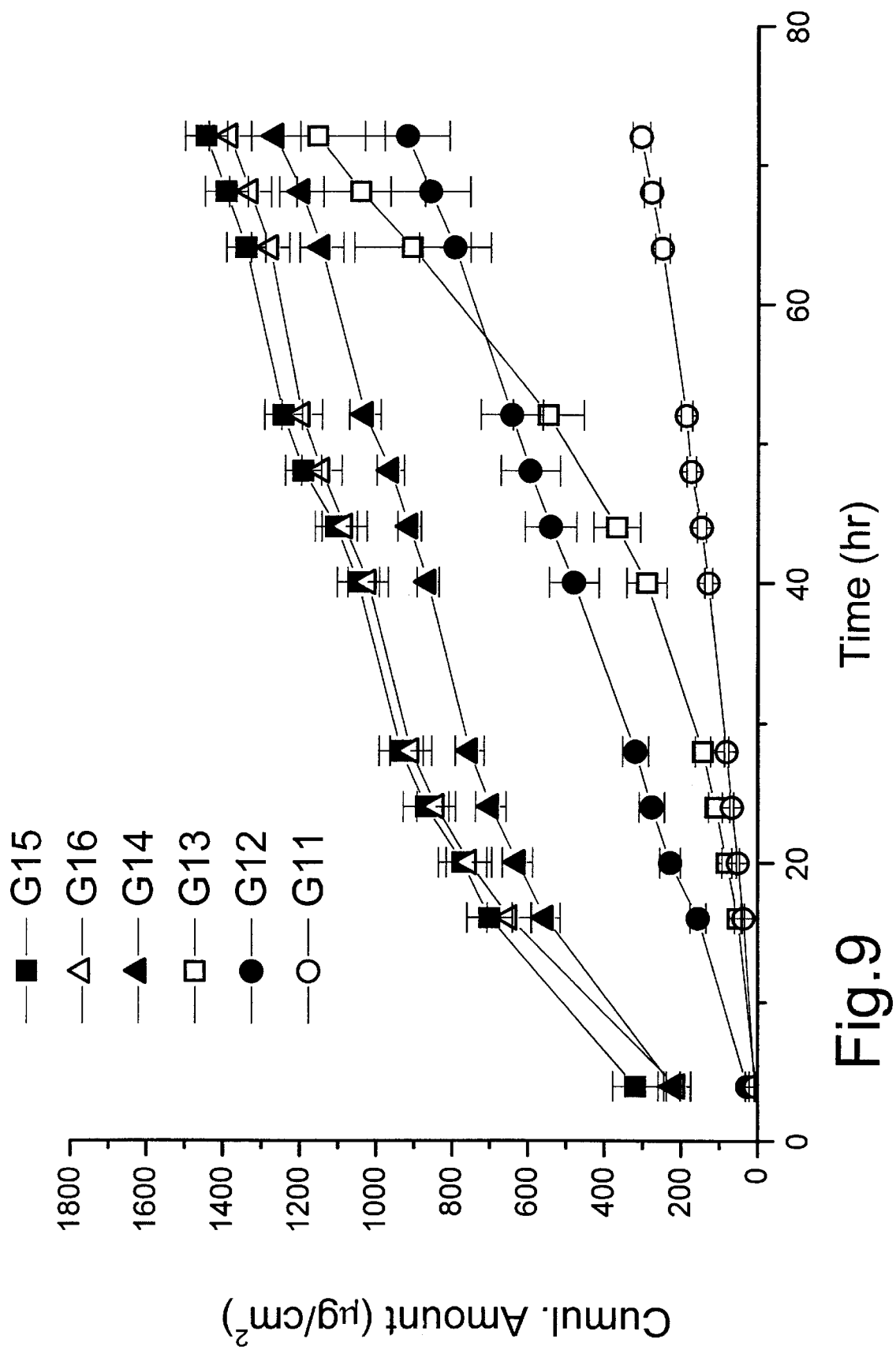
Figure 10:
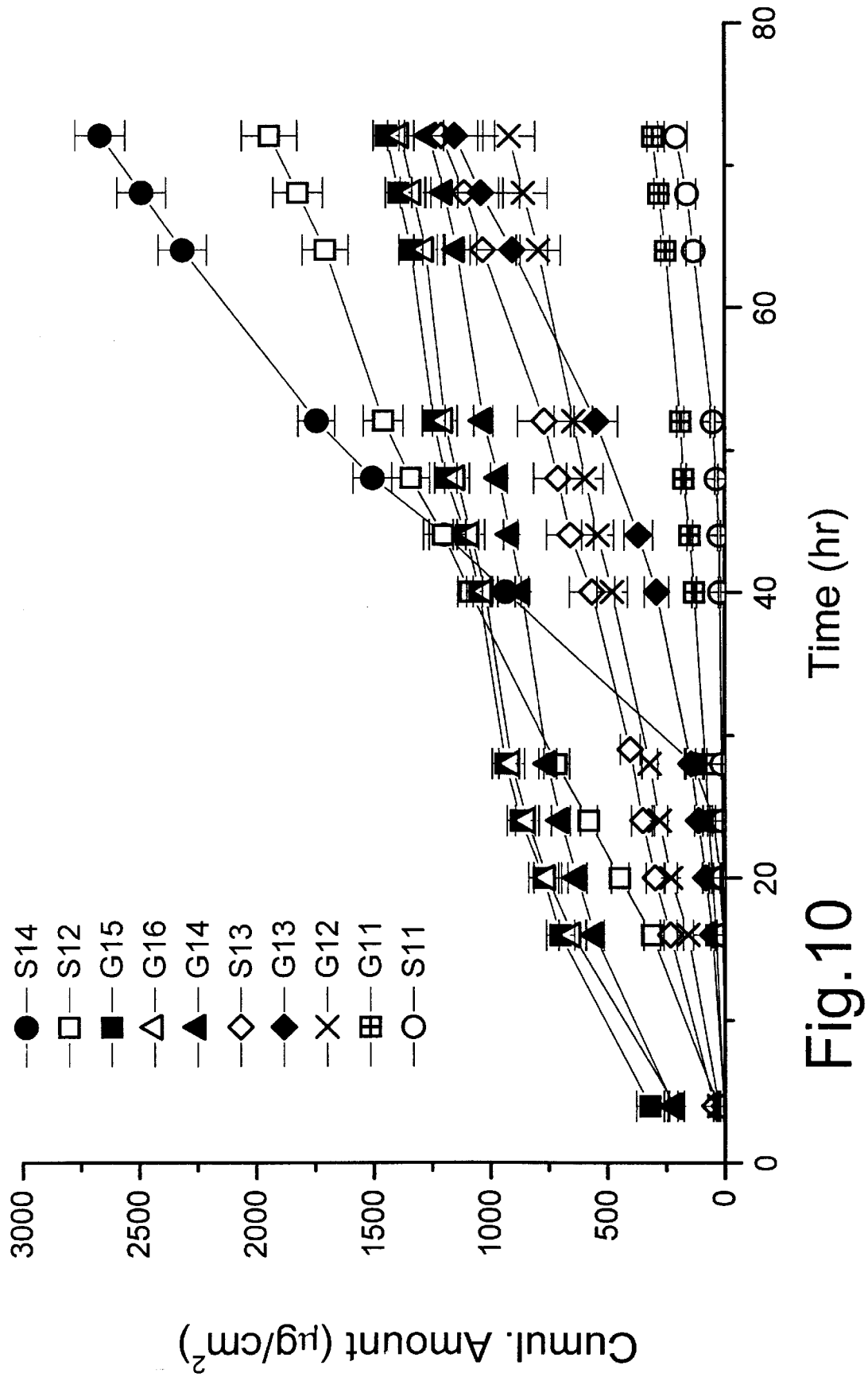
Figure 11:
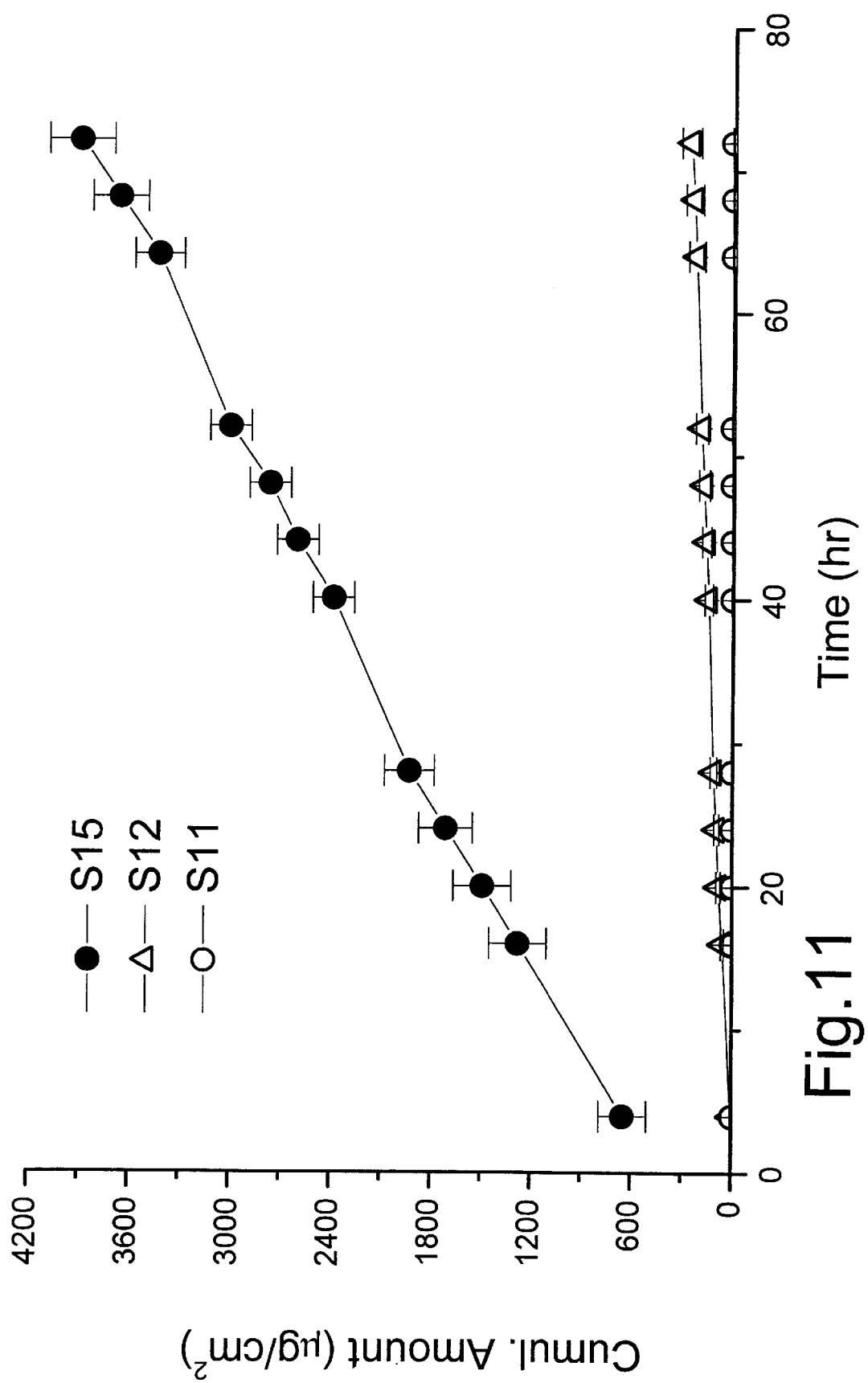
Figure 12:
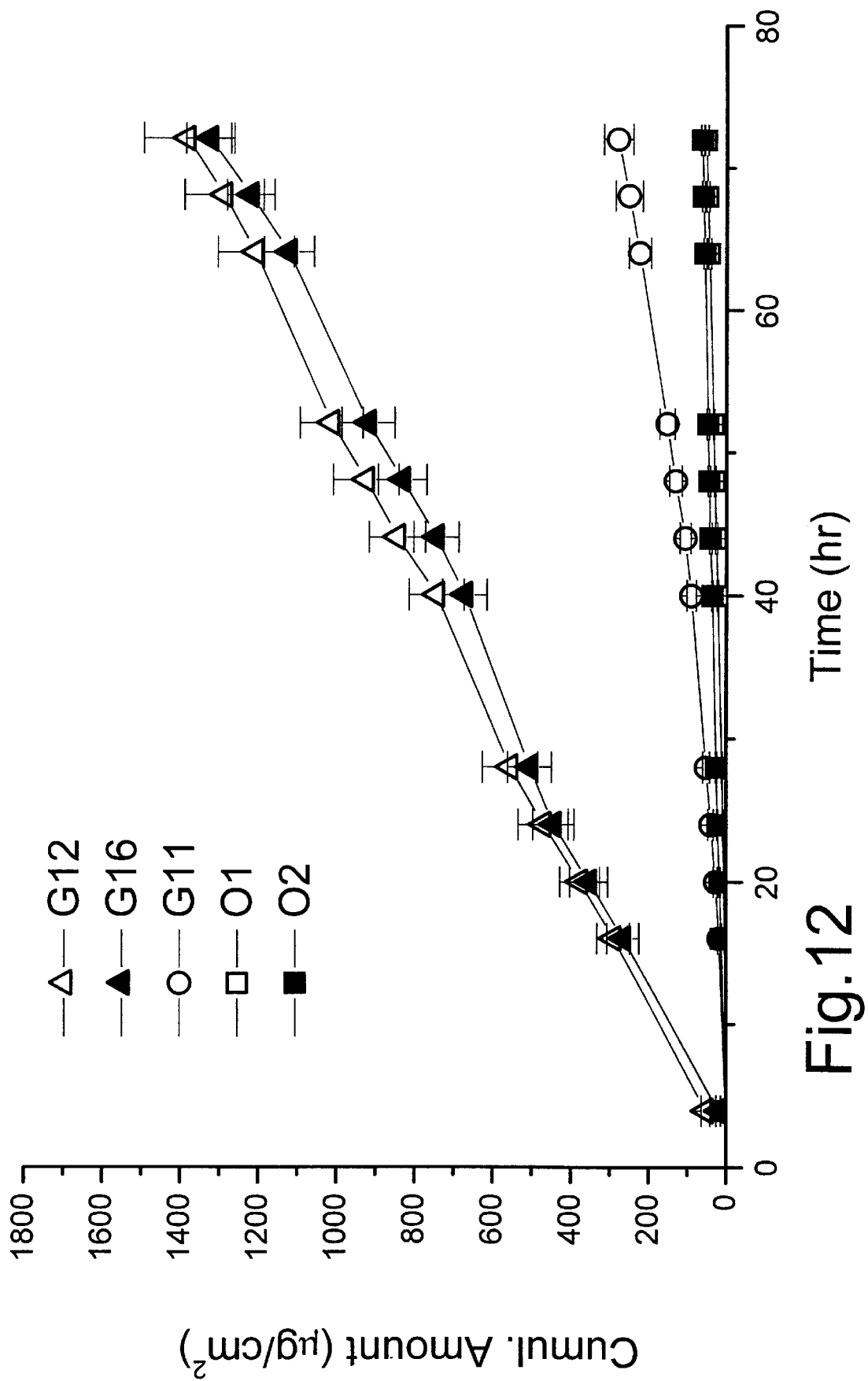
Figure 13:
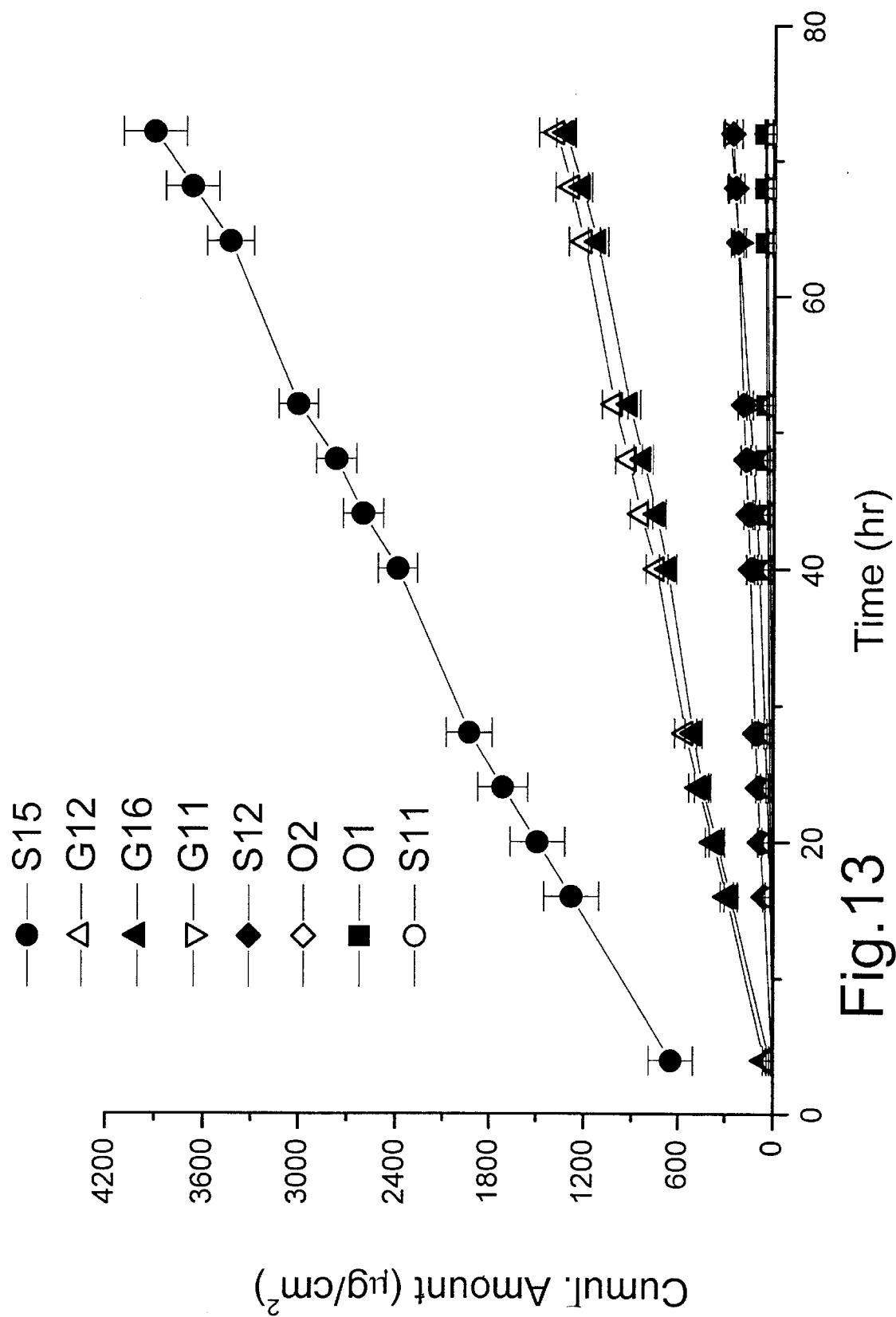
Figure 14:
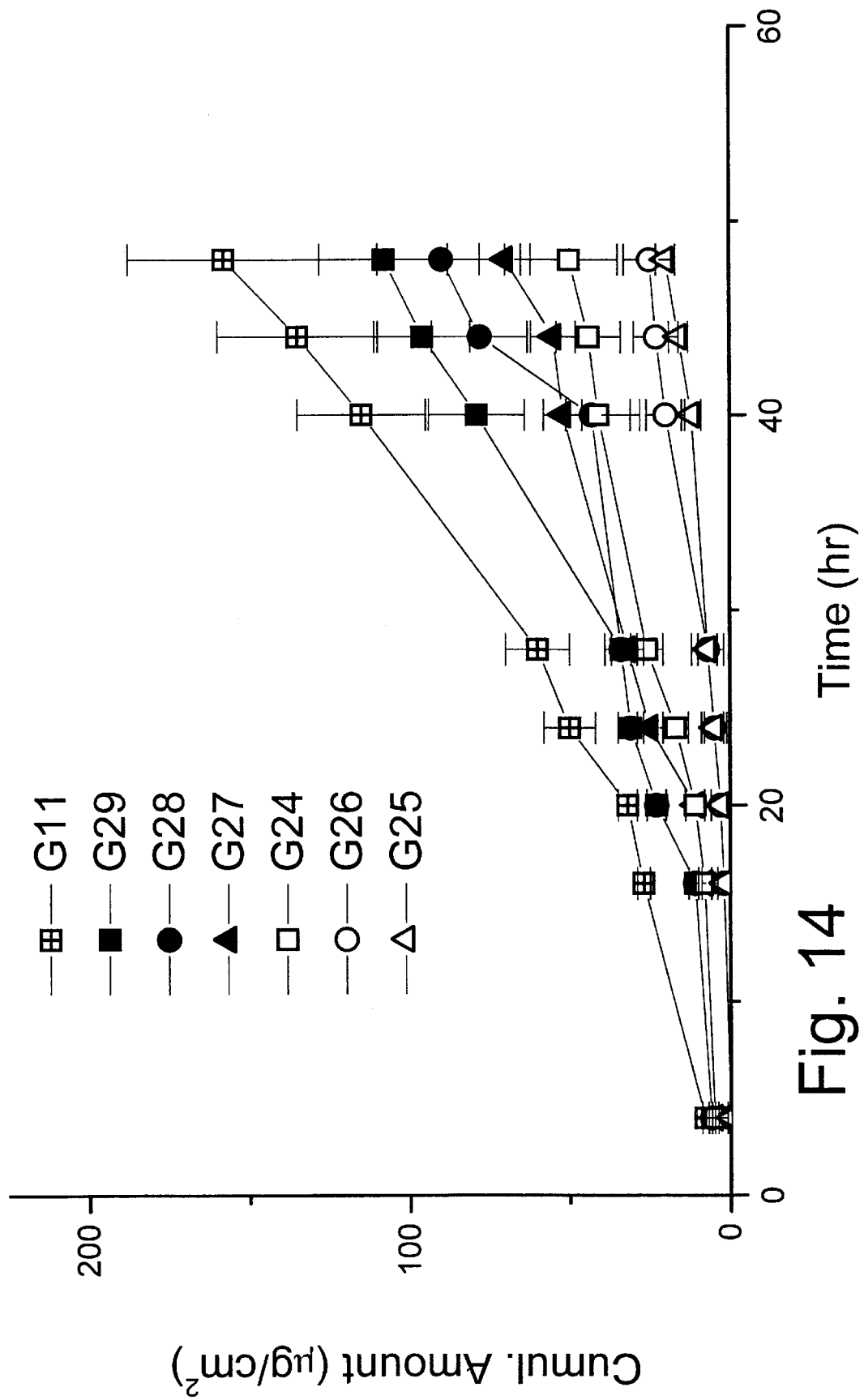
Figure 15:
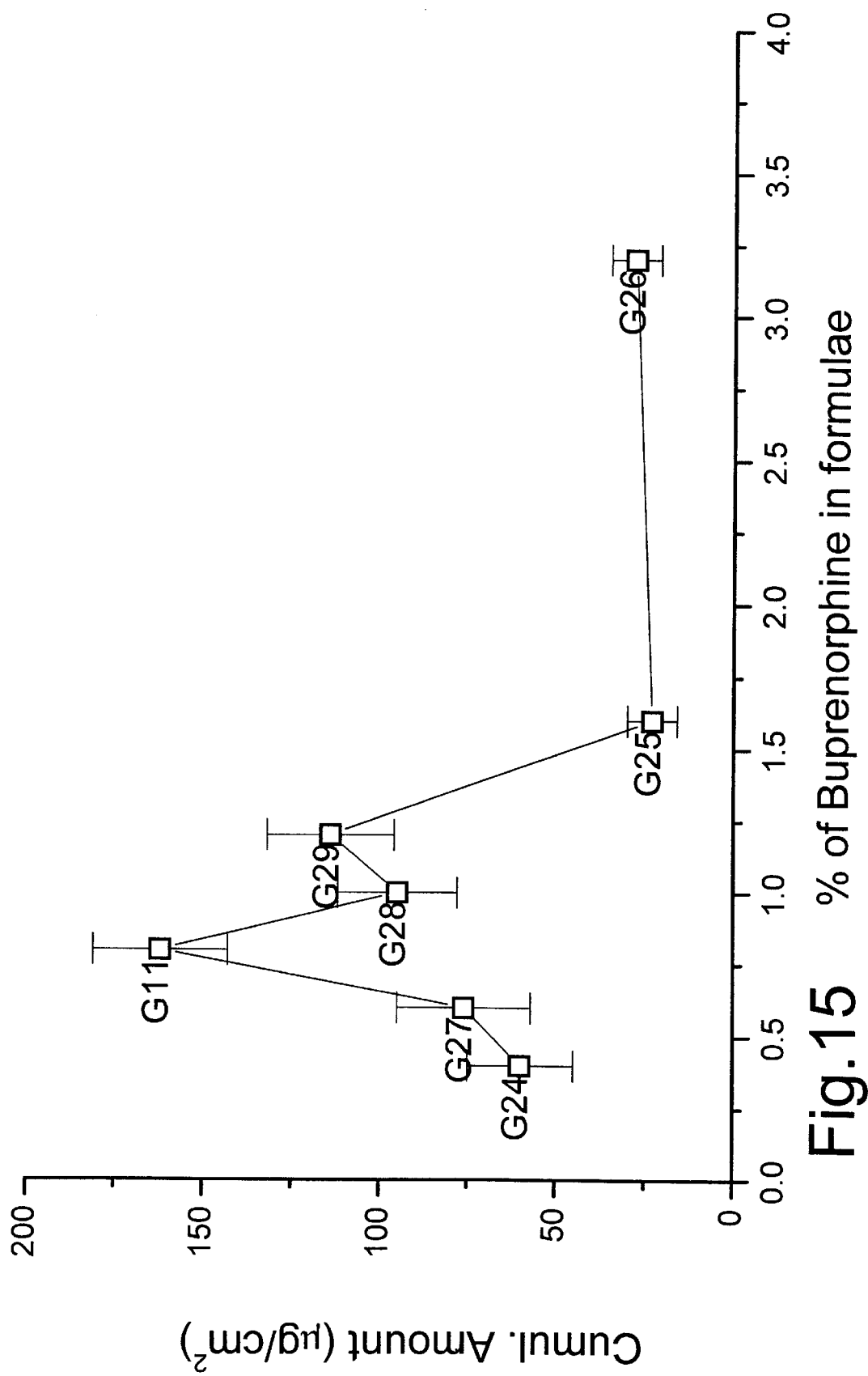
Figure 16:
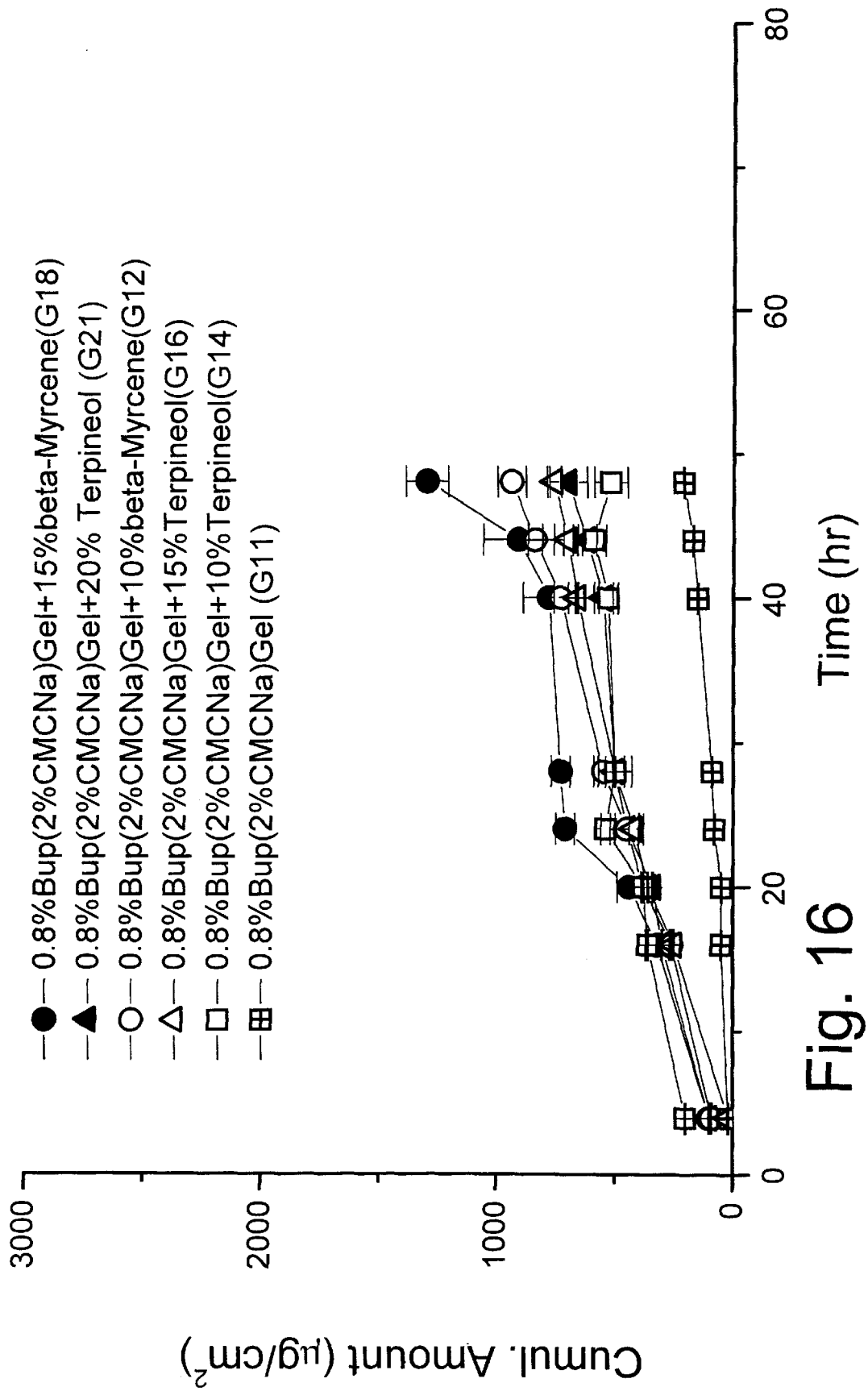
Figure 17:
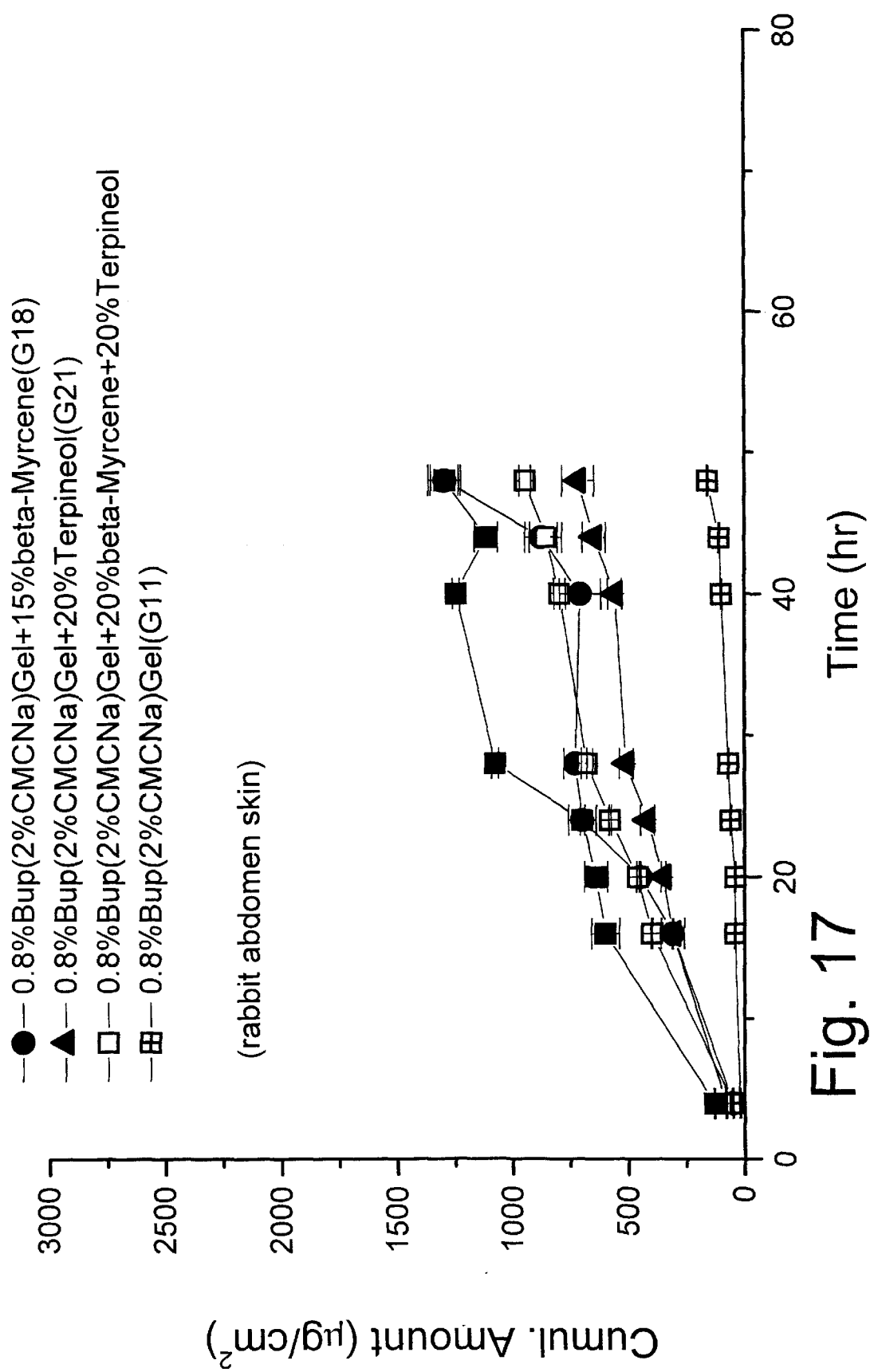

G18 . . . 15% w/w β-myrcene
G21 . . . 20% w/w terpineol
G12 . . . 10% w/w β-myrcene
G16 . . . 15% w/w terpineol
G14 . . . 10% w/w terpineol
G11 . . . control FIG. 17. Penetration of buprenorphine HCl gels in 1,3-propylene glycol and sodium carboxymethylcellulose through the skin of rabbits.

Figure 18:
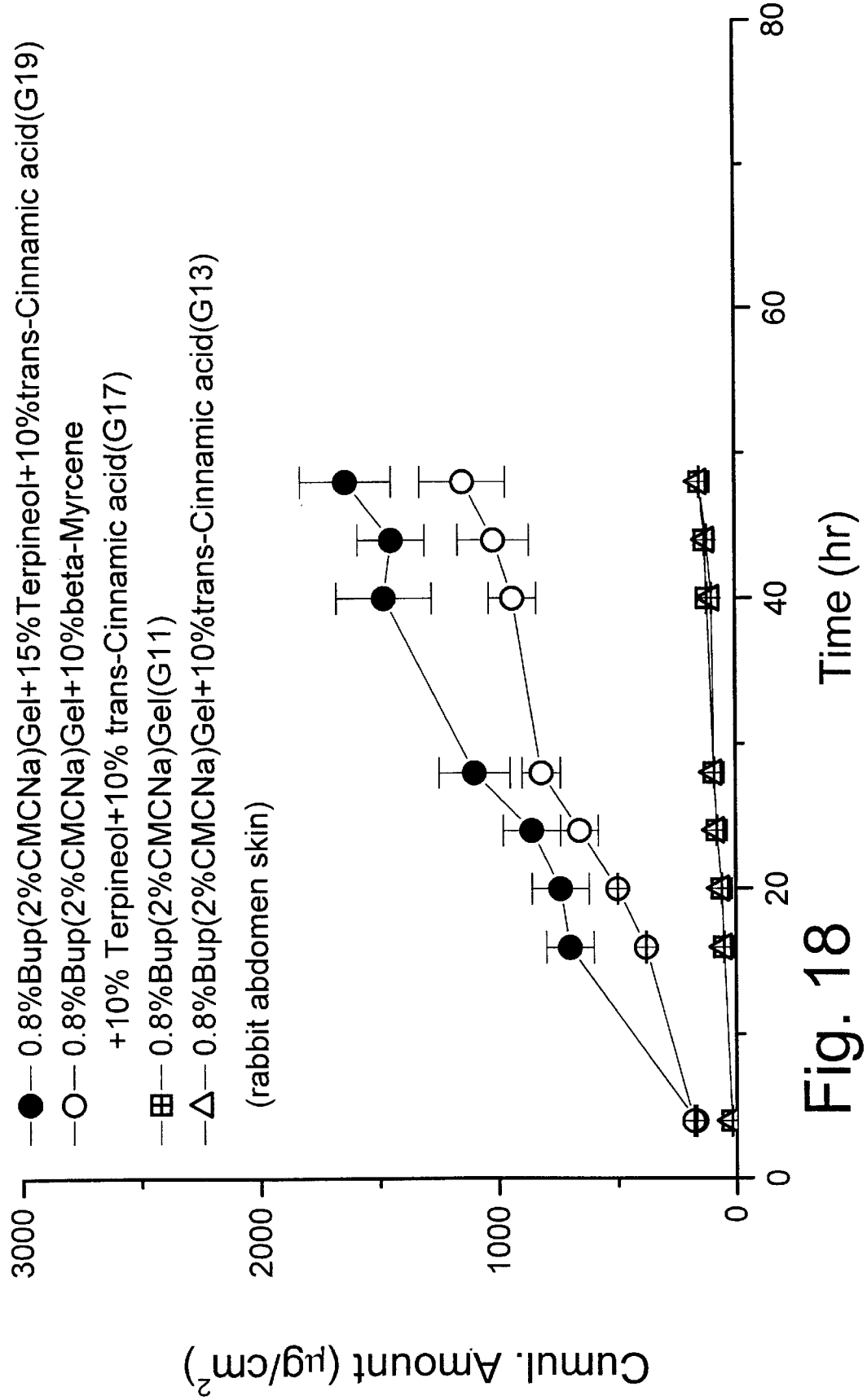
Figure 19:
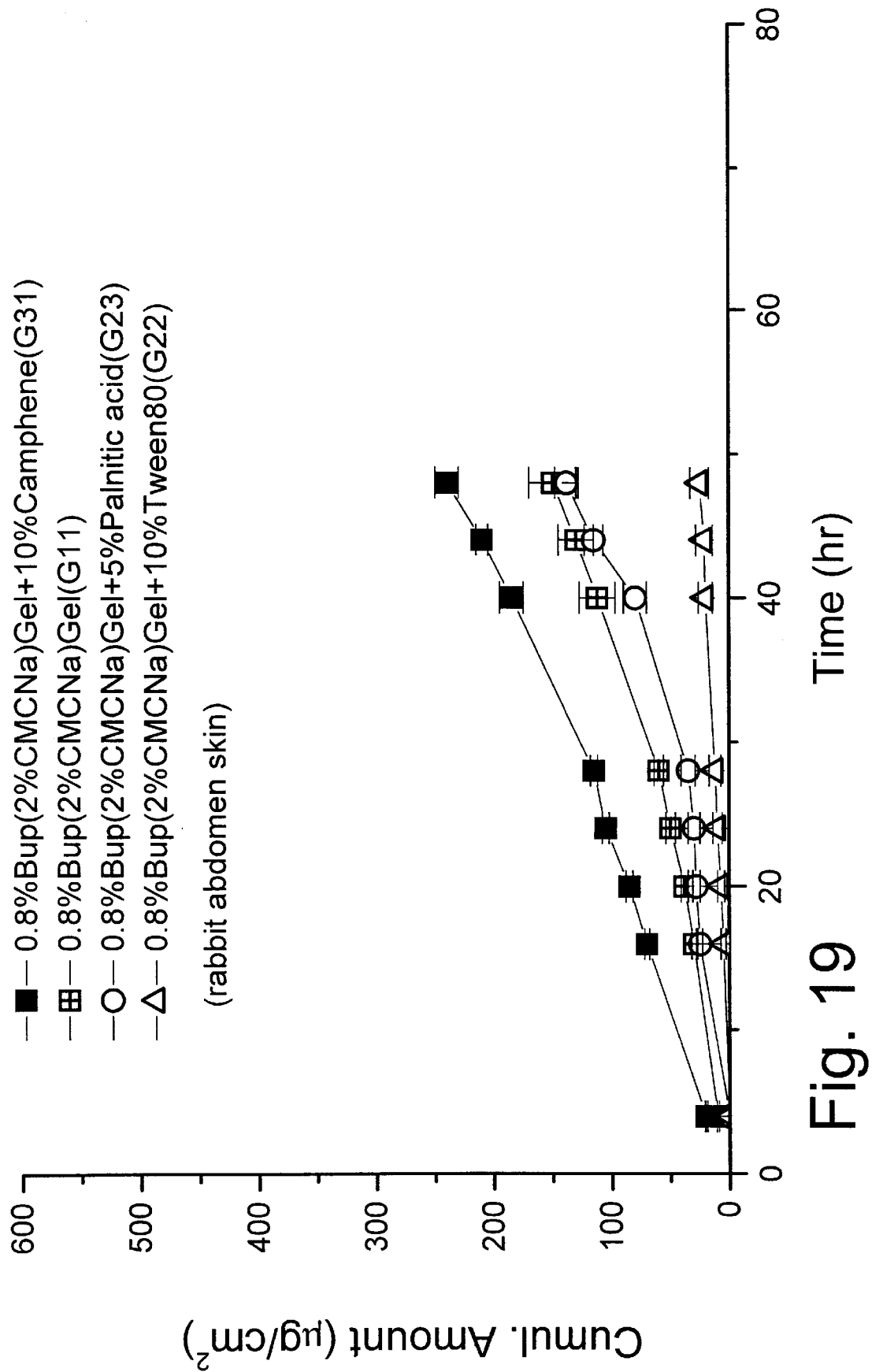

G20 . . . 15% w/w β-myrcene and 15% w/w terpineol
G18 . . . 15% w/w β-myrcene
G21 . . . 20% w/w terpineol
G30 . . . 20% wlw β-myrcene and 20% w/w terpineol
G11 . . . control FIG. 18. Penetration of buprenorphine HCl gels in 2% sodium carboxymethylcellulose through the skin of rabbits G19 . . . 10% w/w terpineol and 10% w/w trans-cinnamic acid
G17 . . . 10% w/w β-myrcene, 10% w/w terpineol, and 10% w/w trans-cinnamic acid
G11 . . . control
G13 . . . 10% w/w trans-cinnamic acid FIG. 19. Penetration of buprenorphine HCl gels in 2% sodium carboxymethylcellulose through the skin of rabbits.

G31 . . . 10% w/w camphene
G11 . . . control
G23 . . . 5% w/w palmitic acid
G22 . . . 10% w/w Tween 80

Figure 20:
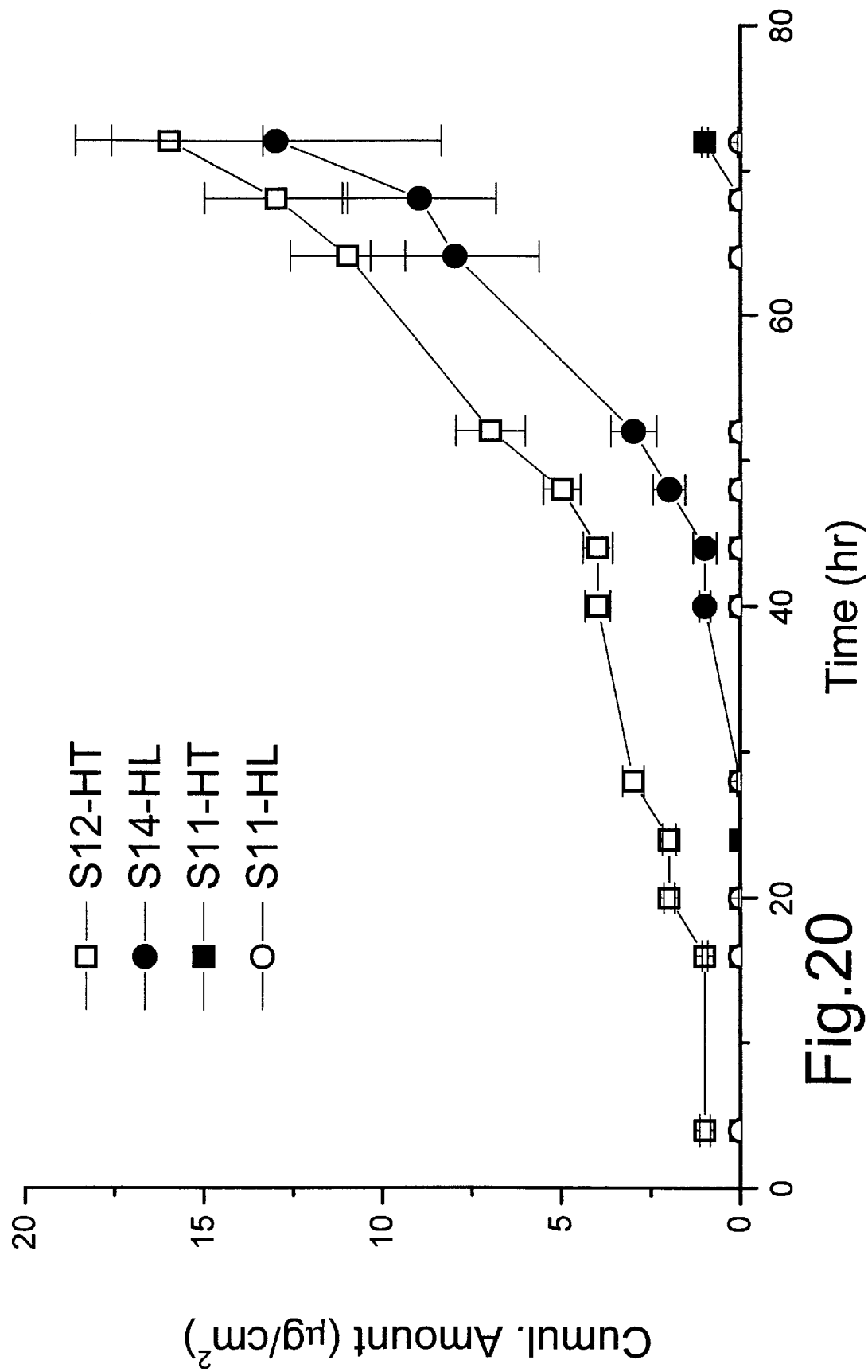

FIG. 20. Penetration of buprenorphine HCl solutions containing enhancers through the skin of human legs.

Figure 21:
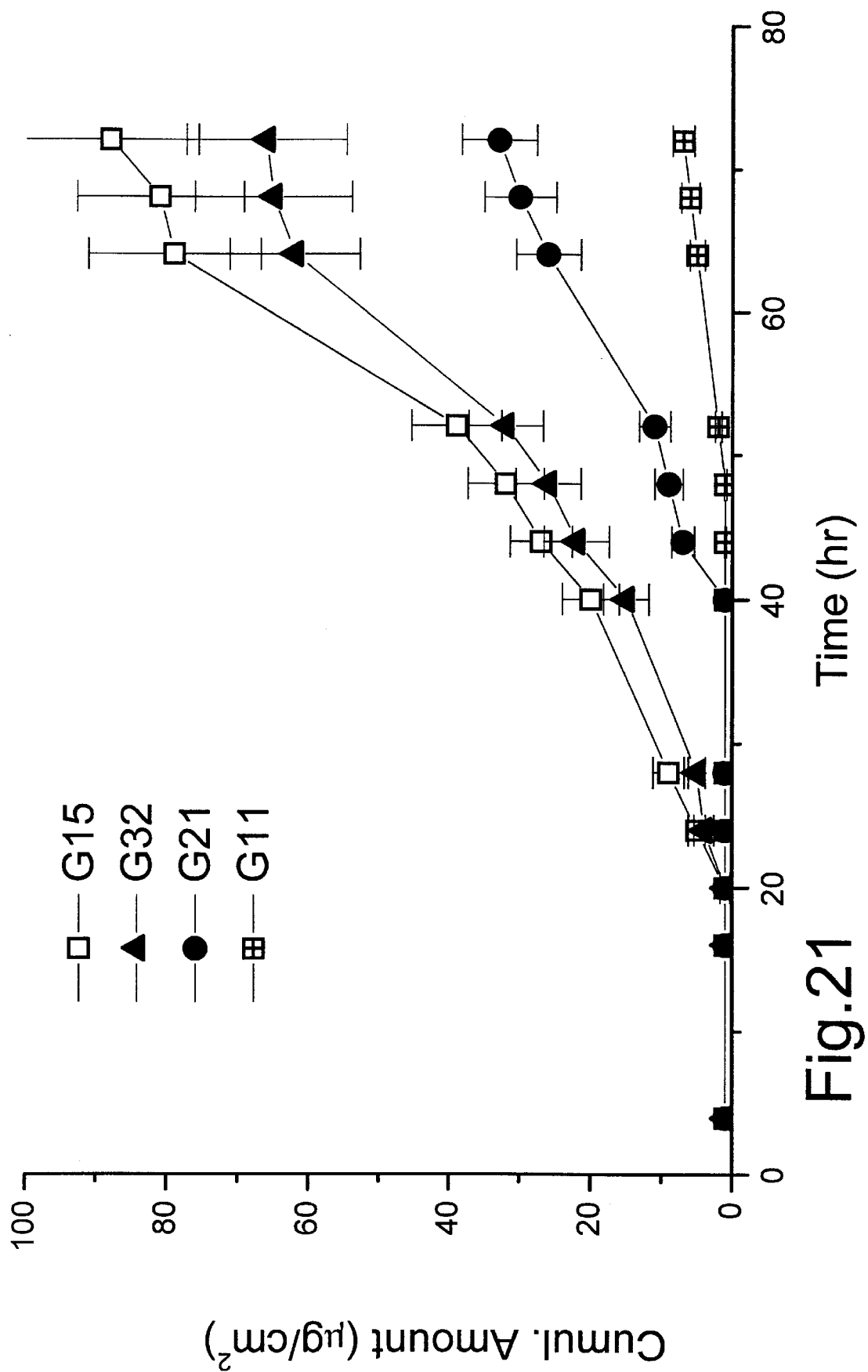
Figure 22:
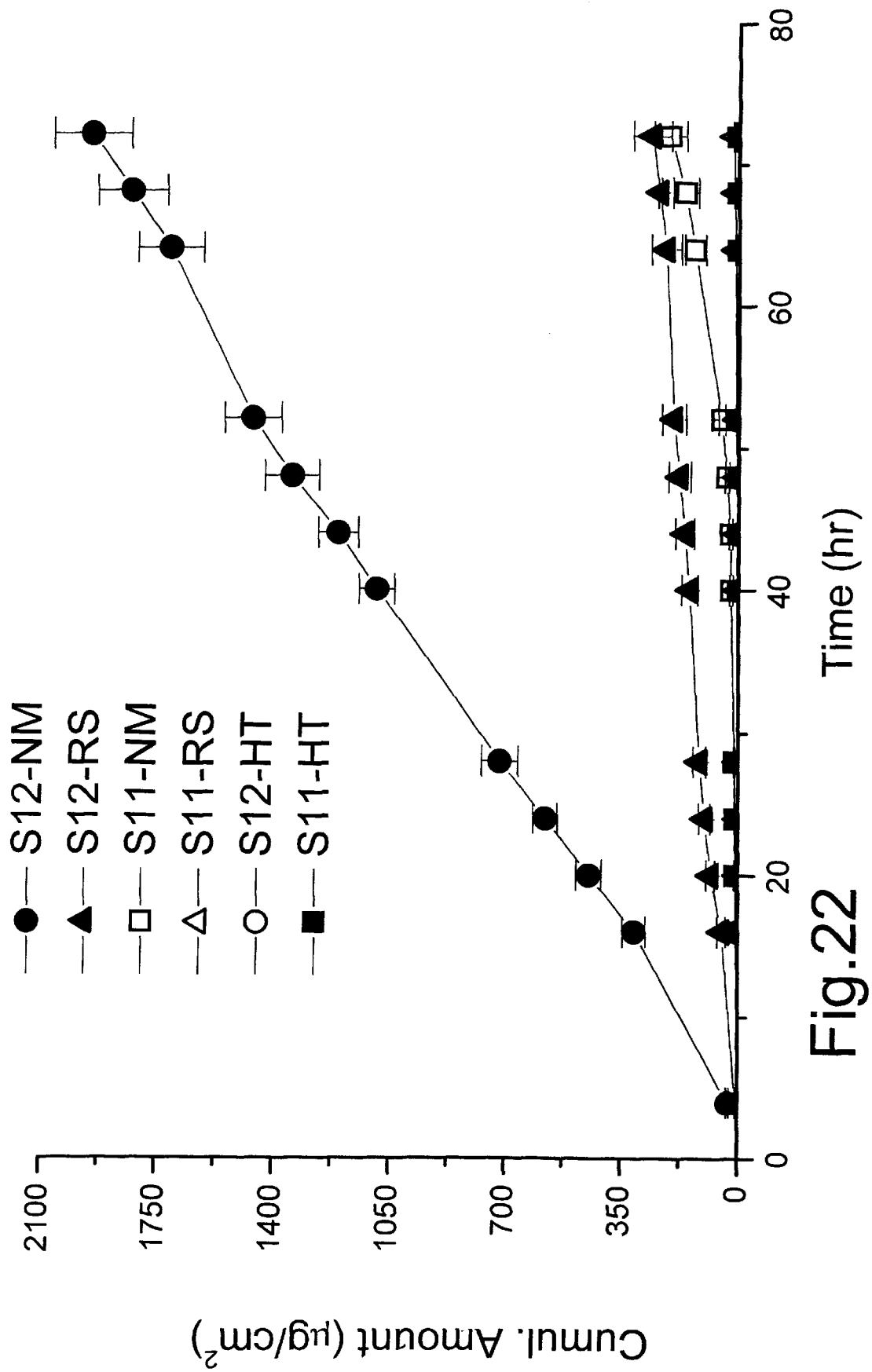

S12-HT . . . 10% w/w β-myrcene/human leg skin
S14-HL . . . 10% w/w terpineol/human foot skin
S11-HT . . . 1,3-propylene glycol/human leg skin
S11-HL . . . 1,3-propylene glycol/human foot skin FIG. 21. Penetration of buprenorphine HCl gels in 2% sodium carboxymethylcellulose through the skin of human chest G15 . . . 10% w/w β-myrcene and 10% w/w terpineol
G32 . . . 20% w/w β-myrcene
G21 . . . 20% w/w terpineol
G11 . . . control FIG. 22. Penetration of buprenorphine HCl in 1,3-propylene glycol solution through different types of skin.

S12-NM . . . 10% w/w β-myrcene/skin of nude mice
S12-RS . . . 10% w/w β-myrcene/skin of rabbits
S11-NM . . . 1,3-propylene glycol/skin of nude mice
S11-RS . . . 1,3-propylene glycol/skin of rabbits
S12-HT . . . 10% w/w β-myrcene/skin of human leg
S11-HT . . . 1,3-propylene glycol/skin of human leg

TABLE 1

Chemistry of Morphine and Related Opioids.
The structure of morphine is as follows:

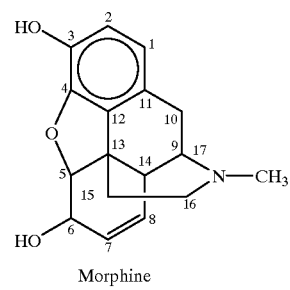

Morphine

| NONPROPRIETARY NAME | CHEMICAL RADICALS AND POSITIONS | | | OTHER CHANGES |
|---|---|---|---|---|
| | 3 | 6 | 17 | |
| Morphine | —OH | —OH | —CH$_3$ | — |
| Heroin | —OCOCH$_3$ | —OCOCH$_3$ | —CH$_3$ | — |
| Hydromorphone | —OH | =O | —CH$_3$ | (1) |
| Oxymorphone | —OH | =O | —CH$_3$ | (1), (2) |
| Levorphanol | —OH | —H | —CH$_3$ | (1), (3) |
| Levaflorphan | —OH | —H | —CH$_2$CH=CH$_2$ | (1), (3) |
| Codeine | —OCH$_3$ | —OH | —CH$_3$ | — |
| Hydrocodone | —OCH$_3$ | =O | —CH$_3$ | (1) |
| Oxycodone | —OCH$_3$ | =O | —CH$_3$ | (1), (2) |
| Nalmefene | —OH | =CH$_2$ | —CH$_2$—◁ | (1), (2) |
| Nalorphine | —OH | —OH | —CH$_2$CH=CH$_2$ | — |
| Naloxone | —OH | =O | —CH$_2$CH=CH$_2$ | (1), (2) |

TABLE 1-continued

Chemistry of Morphine and Related Opioids.
The structure of morphine is as follows:

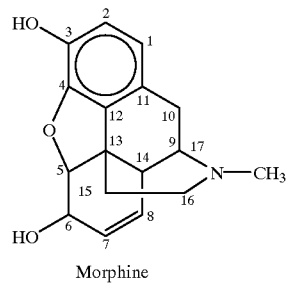

Morphine

| NONPROPRIETARY NAME | CHEMICAL RADICALS AND POSITIONS | | | OTHER CHANGES |
|---|---|---|---|---|
| | 3 | 6 | 17 | |
| Naltrexone | —OH | =O | —CH$_2$—▷ | (1), (2) |
| Buprenorphine | —OH | —OCH$_3$ | —CH$_2$—▷ | (1), (2), (4) |
| Butorphanol | —OH | —H | —CH$_2$—◇ | (2), (3) |
| Nalbuphine | —OH | —OH | —CH$_2$—◇ | (1), (2) |

TABLE 2

| | |
|---|---|
| *Glycyrrhizae Radix* | Glycyrrhizin, glycyrrhetinic acid, 18-β-glycyrrhetinic acid |
| *Zingiberis Rhizoma* | α-Pinene, β-Myrcene, Cineole |
| *Zizyphi Fructus* | Oleanolic acid, Ursolic acid, Zizyphus saponin I, Zizyphus saponin II, Zizyphus saponin III, Jujuboside B, Maslinic acid, Betulonic acid |
| *Cinnamoni Cortex et caulis* | Cinnamaldehyde, Cinnamyl acetate, Phenylpropyl acetate, Cinnzeylanol, Cinnzeylanine, Anhydrocinnzeylanine, Cinncassiol A, Cinncassiol B, Cinncassiol C1, C2, C3, Cinncassiol A 19-monoacetate, Cinncassiol D1, D2, D3, D4, E, Cinncassiol A 19-O-Glucoside, Cinncassiol D1 19-O-Glucoside, Cinncassiol B 19-O-Glucoside, Cinncassiol D2 19-O-Glucoside, Cinncassiol C1 19-O-Glucoside, Anhydrocinnzeylanol, Gallic acid, Procyanidin C-1, B-2, B-5, Apigenin 3,7-dirhamnoside, Protocatechuic acid, (-)-Epicatechin |
| *Cardamomi Fructus* | (+)-α-Terpinyl acetate, 1,8-Cineole, Sabinene, Limonene, (+)-α-Terpineol |
| *Magnoliae Cortex* | β-Eudesmol, α-Pinene, β-Pinene, Camphene, Bornylacetate, Caryophylleneepoxide, Cryptomeridiol, Limonene, Magnolol, Honokiol, Magnocurarine, Magnoflorine, Anonaine, Liriodenine, Salicifoline, α-Eudesmol, Michelarbine |
| *Myristicae Semen* | (+)-Camphene, (+)-Linalool, Safrole, Eugenol, Myristicin, (+)-α-Pinene, (+)-β-Pinene, (+)-Limonene, Xylan, (+)-Borneol, Geraniol, α-Terpineol, Myristin olein, Pentosan, Furfural, Pectin, Lipase, Saponin |
| *Amomi Cardamomi Fructus* | (+)-Camphor, (+)-Borneol, Humulene epoxide, 1,8-Cineole, α-Pinene, β-Pinene, Caryophyllene, Myrcene, Babinene, Humulene, Carvone |

TABLE 3

| | |
|---|---|
| *Cinae Flos* | (−)-α-Pinene, Terpinene, Terpineol, Carvacrol, α-Thujone, (−)-Camphor |
| *Valerianae Radix* | (+)-Bornylisovalerate, Bornylacetate, Kessane, (−)-Camphene, (±)-Limonene, α-Terpineol, α-Kessylalcohol, α-Kessylalcohol acetate, Kessanol, Kessoglycol, Valeranone, Fauronyl acetate, Cryptofauronol, Kanokoonyl acetate, Linalool, β-Pinene, Kanokonol, α-Pinene |
| *Menthae Herba* | (−)-Menthol, Acetyllmenthol, (−)-Menthone, (−)-Limonene, |

TABLE 3-continued

| | |
|---|---|
| | (+)-Menthol, Pulegone, Piperitone, Isomenthone, Camphene, 3-Octanol, γ-Hexenyl, Penylacetate, α-Pinene, Menthenone |
| Perillae Herba | (−)-Perillaldehyde, (+)-Limonene, α-Pinene, Perillaketone, Naginataketone, Egomaketone |
| Corni Fructusus | Oleanolic acid, Ursolic acid, Isoterchebin, Tellimagrandin I, Tellimagrandin II, Gemin D, Corrnusiin A, Cornusiin B, Triogalloyl-β-D-glucose |
| Benzoinum | trans-Cinnamic acid, Benzoic acid |
| Foeniculi Fructus | Anethole, Estragole, (+)-α-Pinene, (+)-Fenchone, (±)-Limonen, Anisaldehyde |
| Achyranthis Radix | Oleanolic acid glycoside |
| Eucalypti Folium | 1,8-Cineole; p-Cymene, Terpineol, Cuminal, Phellandral, Pinene |
| Zanthoxyli Fructus | Genraniol, Limonene, Cumic alcohol, Terpineol |
| Asari Herba cum Radice | Eucarvone, Safrole, Methyleugenol, Elemicin, Asaricin, β-Pinene, (+)-Borneol, Croweacin |
| Piperis Fructus | (−)-α-Phellandrene, β-Pinene, Linalool |

TABLE 4

| | |
|---|---|
| Magnoliae Flos | Methylchavicol, Camphor, 1,8-Cineole, ρ-Cymene |
| Lupuli Strobilus | α-Humulene, β-humulene, Humuladienone, α-Corocalene, meta-Camphorene, Paracamphorene, Myrcene |
| Zedoariae Rhizoma | Curzerenone, Curdione, Curcolone, Furanodienone, Furanogermenone, 1,4-Cineole, Zederone, Curcumol |
| Bupleuri Radix | Saikosaponin a, c, d, Oleic acid, α-Spinasterol, Δ7-Stigmasterol, Linolenic acid, Lignoceric acid, Adonitol, Saikogenin F, E, G, Longispinogenin, Lignoceric acid, Palmitic acid, Angelicin, Stearic acid |
| Mori Radicis Cortex | α-amyrin, Stearic acid, Palmitic acid, Kuwanon A ~ H, P, Q, R, V, S, T, Albanol B, Moracenin C, D |
| Coicis Semen | Stearic acid, Palmitic acid, Oleic acid, Coixans A, B, C |

TABLE 5

| Code | Buprenorphine | 1,3-PEG | Triethanolamine | β-myrcene | Capric acid | Cineole | (+)-α-Pinene | β-glycyrrhetinic acid | Transinnalmaldehyde | Oleanolic acid | H2O |
|---|---|---|---|---|---|---|---|---|---|---|---|
| S1 | 1.22 | 100 | | | | | | | | | |
| S2 | 0.878 | 90 | | 10 | | | | | | | |
| S3 | 0.992 | 90 | | | 10 | | | | | | |
| S4 | 1.077 | 90 | | | | 10 | | | | | |
| S5 | 1.34 | 90 | | | | | 10 | | | | |
| S6 | 1.917 | 100 | | | | | | 2 | | | |
| S7 | 0.884 | 90 | | | | | | | 10 | | |
| S8 | 0.309 | 100 | | | | | | | | 2 | |
| S9 | 0.127 | | | | | | | | | | 100 |
| S10 | 0.118 | | | | | | | | | | 100 |

TABLE 6

| Code | Buprenorphine (mg/ml) | Glycerin (%) | 1,3-PEG (%) | Sodium CMC (mg/ml) | Water (%) |
|---|---|---|---|---|---|
| G1 | 1 | 50 | | 20 | 50 |
| G2 | 1.5 | 50 | | 20 | 50 |
| G3 | 2 | 50 | | 20 | 50 |
| G4 | 2.5 | 50 | | 20 | 50 |
| G5 | 1 | 45 | 5 | 20 | 50 |
| G6 | 1 | 40 | 10 | 20 | 50 |
| G7 | 1 | 30 | 20 | 20 | 50 |
| G8 | 1 | 0 | 50 | 20 | 50 |
| G9 | 1 | 0 | 60 | 20 | 40 |
| G10 | 1 | 0 | 70 | 20 | 30 |

TABLE 7

| Code | Buprenorphine (mg/ml) | Oil of olay base (%) | 1,3-PEG (%) |
|---|---|---|---|
| E1 | 1 | 90 | 10 |
| E2 | 1 | 80 | 20 |
| E3 | 1 | 70 | 30 |
| E4 | 1 | 60 | 40 |

TABLE 8

| Formula | S11 | S12 | S13 | S14 | S15 | O1 | O2 | G11 | G12 | G13 | G14 | G15 | G16 |
|---|---|---|---|---|---|---|---|---|---|---|---|---|---|
| Buprenorphine (%) | 0.8 | 0.8 | 0.8 | 0.8 | 0.8 | 0.8 | 0.8 | 0.8 | 0.8 | 0.8 | 0.8 | 0.8 | 0.8 |
| Propylene Glycol (PG) (%) | 100 | 90 | 85 | 90 | 80 | 74.5 | 64.5 | 20 | 20 | 20 | 20 | 20 | 20 |
| Stearyl Alcohol (%) | | | | | | 18.6 | 18.6 | | | | | | |
| Cetyl Alcohol (%) | | | | | | 6.19 | 6.19 | | | | | | |
| CMC Na (%) | | | | | | | | 2 | 2 | 2 | 2 | 2 | 2 |
| Water (%) | | | | | | | | 77.2 | 67.2 | 67.2 | 67.2 | 57.2 | 62.2 |
| β-Myrcene (%) | | 10 | 15 | | 10 | | 10 | | 10 | | | 10 | |
| Terpineol (%) | | | | 10 | 10 | | | | | | 10 | 10 | 15 |
| trans-Cinnamic acid (%) | | | | | | | | | | 10 | | | |

TABLE 9

| Constituents | G17 | G18 | G19 | G20 | G21 | G22 | G23 | G24 | G25 | G26 | G27 | G28 | G29 | G30 | G31 | G32 |
|---|---|---|---|---|---|---|---|---|---|---|---|---|---|---|---|---|
| Buprenorphine | 0.8 | 0.8 | 0.8 | 0.8 | 0.8 | 0.8 | 0.8 | 0.4 | 1.6 | 3.2 | 0.6 | 1.0 | 1.2 | 0.8 | 0.8 | 0.8 |
| Sodium CMC | 2 | 2 | 2 | 2 | 2 | 2 | 2 | 2 | 2 | 2 | 2 | 2 | 2 | 2 | 2 | 2 |
| Propylene Glycol | 20 | 20 | 20 | 20 | 20 | 20 | 20 | 20 | 20 | 20 | 20 | 20 | 20 | 20 | 20 | 20 |
| β-Myrcene | 10 | 15 | | 15 | | | | | | | | | | 20 | | 20 |
| trans-Cinnamic acid | 10 | | 10 | | | | | | | | | | | | | |
| α-Terpineol | 10 | | 10 | 15 | 20 | | | | | | | | | 20 | | |
| Camphene | | | | | | | | | | | | | | | 10 | |
| Palmitic acid | | | | | | | 5 | | | | | | | | | |
| Tween 80 | | | | | | 20 | | | | | | | | | | |
| Water | 47.2 | 62.2 | 57.2 | 47.2 | 57.2 | 57.2 | 72.2 | 77.6 | 76.4 | 74.8 | 77.4 | 77 | 76.8 | 37.2 | 67.2 | 57.2 |

TABLE 10

| | | 48 hr | | | |
|---|---|---|---|---|---|
| Formula | n = | C.A.(μg/ml) | SE | ratio | rank |
| S 1 | 6 | 57 | 9 | 1.0 | 9 | |
| S 2 | 6 | 450 | 59 | 7.9 | 1 | *** |
| S 3 | 6 | 133 | 30 | 2.3 | 4 | * |
| S 4 | 6 | 58 | 8 | 1.0 | 8 | |
| S 5 | 6 | 260 | 19 | 4.6 | 2 | *** |
| S 6 | 6 | 13 | 3 | 0.2 | 10 | |
| S 7 | 6 | 138 | 22 | 2.4 | 3 | * |
| S 8 | 6 | 93 | 24 | 1.6 | 7 | |
| S 9 | 6 | 127 | 16 | 2.2 | 5 | * |
| S 10 | 6 | 94 | 12 | 1.7 | 6 | |
| S 11 | 16 | 35 | 7 | 1.0 | 4 | |
| S 12 | 6 | 1415 | 102 | 40.4 | 2 | *** |
| S 13 | 6 | 711 | 105 | 20.3 | 3 | *** |
| S 14 | 4 | 1546 | 82 | 44.2 | 1 | *** |
| G 1 | 6 | 110 | 8 | 1.0 | 4 | |
| G 2 | 6 | 167 | 18 | 1.5 | 3 | |
| G 3 | 6 | 389 | 53 | 3.5 | 2 | ** |
| G 4 | 6 | 604 | 101 | 5.5 | 1 | *** |
| G 1 | 6 | 134 | 30 | 1.0 | 5 | |
| G 5 | 6 | 113 | 14 | 0.8 | 7 | |
| G 6 | 6 | 115 | 22 | 0.9 | 6 | |
| G 7 | 6 | 145 | 20 | 1.1 | 4 | |
| G 8 | 6 | 159 | 21 | 1.2 | 3 | |
| G 9 | 6 | 196 | 11 | 1.5 | 2 | * |
| G 10 | 6 | 203 | 13 | 1.5 | 1 | ** |
| G 11 | 16 | 175 | 12 | 1.0 | 6 | |
| G 12 | 6 | 596 | 78 | 3.4 | 4 | *** |
| G 13 | 6 | 369 | 61 | 2.1 | 5 | *** |
| G 14 | 6 | 965 | 35 | 5.5 | 3 | *** |
| G 15 | 6 | 1193 | 48 | 6.8 | 1 | *** |
| G 16 | 6 | 1145 | 53 | 6.5 | 2 | *** |
| E 1 | 6 | 64 | 1 | 1.00 | 3 | *** |
| E 2 | 6 | 54 | 4 | 0.84 | 5 | *** |
| E 3 | 6 | 58 | 5 | 0.91 | 4 | *** |
| E 4 | 6 | 67 | 5 | 1.04 | 2 | *** |
| E 5 | 6 | 86 | 11 | 1.35 | 1 | *** |
| E 6 | 6 | 10 | 1 | 0.16 | 6 | |

***p < 0.001
**p < 0.01
*p < 0.05

TABLE 11

| | | 48 hr | | | |
|---|---|---|---|---|---|
| Formula | n = | C.A.(μg/ml) | SE | ratio | rank |
| S 11 | 8 | 9 | 2 | 1.0 | 3 | |
| S 12 | 6 | 177 | 33 | 19.2 | 2 | * |
| S 15 | 6 | 2768 | 123 | 301.2 | 1 | *** |
| O 1 | 6 | 30 | 3 | 1.0 | 2 | |
| O 2 | 6 | 46 | 3 | 1.5 | 1 | ** |
| G 11 | 44 | 162 | 19 | 1.0 | 11 | |
| G 12 | 6 | 926 | 84 | 5.7 | 6 | *** |
| G 13 | 5 | 116 | 36 | 0.7 | 13 | |
| G 14 | 6 | 583 | 50 | 3.6 | 9 | *** |
| G 16 | 6 | 833 | 62 | 5.1 | 7 | *** |
| G 17 | 5 | 1214 | 192 | 7.5 | 3 | *** |
| G 18 | 5 | 1362 | 93 | 8.4 | 1 | *** |
| G 19 | 6 | 1343 | 226 | 8.3 | 2 | *** |
| G 20 | 6 | 1127 | 42 | 7.0 | 4 | *** |
| G 21 | 5 | 604 | 59 | 3.7 | 8 | *** |
| G 22 | 6 | 115 | 21 | 0.7 | 14 | |
| G 23 | 5 | 138 | 11 | 0.8 | 12 | |
| G 24 | 6 | 60 | 15 | 0.4 | 18 | |
| G 25 | 6 | 23 | 7 | 0.1 | 20 | |
| G 26 | 5 | 28 | 7 | 0.2 | 19 | |
| G 27 | 3 | 76 | 19 | 0.5 | 17 | |
| G 28 | 3 | 95 | 17 | 0.6 | 16 | |
| G 29 | 3 | 114 | 18 | 0.7 | 15 | |
| G 30 | 4 | 1008 | 64 | 6.2 | 5 | *** |
| G 31 | 4 | 250 | 12 | 1.5 | 10 | |

TABLE 11-continued

| | | 48 hr | | | |
|---|---|---|---|---|---|
| Formula | n = | C.A.($\mu$g/ml) | SE | ratio | rank |

***$p < 0.001$
**$p < 0.01$
*$p < 0.05$

TABLE 12

| | | 48 hr | | | | 72 hr | | | | | |
|---|---|---|---|---|---|---|---|---|---|---|---|
| Formula | n = | C.A.($\mu$g/ml) | SE | ratio | rank | C.A.($\mu$g/ml) | SE | ratio | rank | | |
| S 11 | 5 | | ### | | | 1.2 | 0.1 | 1.0 | 2 | | Hum. leg |
| S 12 | 6 | 5.4 | 0.5 | | | 16.4 | 2.6 | 14.1 | 1 | *** | |
| S 11 | 4 | | ### | | | 0.17 | 0.09 | 1.0 | 2 | | Hum. foot |
| S 14 | 4 | 2.0 | 0.4 | | | 13.5 | 4.6 | 81.1 | 1 | * | |
| G 11 | 6 | 1.5 | 0.1 | 1.0 | 4 | 6.7 | 1.5 | 1.0 | 4 | | Hum. chest |
| G 21 | 6 | 9.3 | 2.0 | 6.2 | 3 | 33.0 | 5.4 | 4.9 | 3 | * | |
| G 15 | 6 | 32.3 | 5.4 | 21.6 | 1 | 87.6 | 12.4 | 13.1 | 1 | *** | |
| G 32 | 5 | 25.8 | 4.6 | 17.2 | 2 | 65.8 | 11.3 | 9.8 | 2 | *** | |

***$p < 0.001$
**$p < 0.01$
*$p < 0.05$

What is claimed is:

1. A composition for the transdermal delivery of buprenorphine of formula

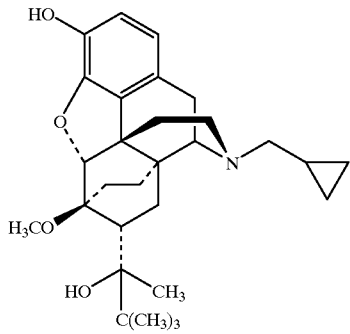

which consists of 1) buprenorphine or the hydrochloride salt thereof in the amount of about 0.8%

2) a drug enhancer in the amount of about 10–20%, said drug enhancer being at least one member selected from the group consisting of 2-pinene, trans-cinnaminc acid, β-myrcene, terpineol, and 3) about 79.2–89.2% of an excipient wh ich is at least one member selected from the group consisting of stearyl alcohol, sodium carboxymethyl-cellulose, glycerol, cetyl alcohol, 1,3-propylene glycol and water.

2. The composition according to claim 1 which is in the form of an ointment, a suspension, a gel, a solution, a cream, a lotion, an emulsion, a plaster or an aerosol.

3. The composition according to claim 2 which consists of buprenorphine hydrochloride, β-myrcene or terpineol or a mixture thereof as the enhancer and 1,3-propylene glycol as the excipient in the form of a gel.

4. The composition according to claim 3 wherein a mixture of β-myrcene and terpineol is the enhancer.

5. A method of transdermally delivering buprenorphine or its hydrochloride salt to a memmal which consists of topically administering a composition consisting of
   1) buprenorphine or the hydrochloride salt thereof in the amount of about 0.8%,
   2) a drug enhancer in the amount of about 10–20% said drug enhancer being at least one member selected from the group consisting of 2-pinene, trans-cinnamic acid, 3-myrcene, terpineol, and
   3) about 792–89.2% of an excipient which is at least one member selected from the group consisting of stearyl alcohol, sodium carboxymethylcellulose, glycerol, cetyl alcohol, 1,3-propylene glycol and water.

6. The method according to claim 5 wherein the excipient is 1,3-propylene glycol.

* * * * *